(12) United States Patent
Steendam et al.

(10) Patent No.: US 9,364,442 B2
(45) Date of Patent: Jun. 14, 2016

(54) BIODEGRADABLE PHASE SEPARATED SEGMENTED MULTI BLOCK CO-POLYMERS AND RELEASE OF BIOLOGICALLY ACTIVE POLYPEPTIDES

(75) Inventors: Rob Steendam, Groningen (NL); Theodorus Adrianus Cornelius Flipsen, Groningen (NL); Christine Hiemstra, Groningen (NL); Johan Zuidema, Aduard (NL)

(73) Assignee: INNOCORE TECHNOLOGIES B.V., Groningen (NL)

( * ) Notice: Subject to any disclaimer, the term of this patent is extended or adjusted under 35 U.S.C. 154(b) by 150 days.

(21) Appl. No.: 13/808,492

(22) PCT Filed: Jul. 8, 2011

(86) PCT No.: PCT/NL2011/050502
§ 371 (c)(1),
(2), (4) Date: Mar. 13, 2013

(87) PCT Pub. No.: WO2012/005594
PCT Pub. Date: Jan. 12, 2012

(65) Prior Publication Data
US 2013/0209568 A1    Aug. 15, 2013

Related U.S. Application Data

(60) Provisional application No. 61/362,710, filed on Jul. 9, 2010.

(51) Int. Cl.
| | | |
|---|---|---|
| A61K 9/50 | (2006.01) | |
| A61K 9/00 | (2006.01) | |
| A61K 9/16 | (2006.01) | |
| A61K 9/70 | (2006.01) | |
| A61K 47/34 | (2006.01) | |
| A61K 38/38 | (2006.01) | |
| A61K 38/47 | (2006.01) | |

(52) U.S. Cl.
CPC ............ *A61K 9/5031* (2013.01); *A61K 9/0024* (2013.01); *A61K 9/1647* (2013.01); *A61K 9/7007* (2013.01); *A61K 38/385* (2013.01); *A61K 38/47* (2013.01); *A61K 47/34* (2013.01); *G01N 2203/0282* (2013.01)

(58) Field of Classification Search
None
See application file for complete search history.

(56) References Cited

U.S. PATENT DOCUMENTS

| | | | |
|---|---|---|---|
| 4,429,080 A | 1/1984 | Casey et al. | |
| 4,643,734 A | 2/1987 | Lin | |
| 5,066,772 A | 11/1991 | Tang et al. | |
| 5,133,739 A | 7/1992 | Bezwada et al. | |
| 5,236,444 A | 8/1993 | Muth et al. | |
| 5,324,519 A * | 6/1994 | Dunn et al. | ........... 424/426 |
| 5,554,170 A | 9/1996 | Roby et al. | |
| 5,980,948 A | 11/1999 | Goedemoed et al. | |
| 6,255,408 B1 | 7/2001 | Shalaby | |
| 2007/0003592 A1* | 1/2007 | Hissink | ........... 424/426 |

FOREIGN PATENT DOCUMENTS

| | | |
|---|---|---|
| EP | 1382628 | 7/2002 |
| EP | 1555278 | 1/2004 |
| WO | 2005/115599 | 12/2005 |
| WO | 2012/005594 | 1/2012 |

OTHER PUBLICATIONS

Loh et al., J. Controlled Release, 2010, 143(2), pp. 175-182.*
Sigma-Aldrich, Product Information for Platelet-Derived Growth Factor, 2012, pp. 1-2.*
Rozema et al., Late Tissue Response to Bone-Plates and Screws of Poly(L-Lactide) used for Fracture Fixation of the Zygomatic Bone, Biomaterial-Tissue Interfaces, p. 349-355 (1992).
Jin Woo Lee et al., Thermoreversible gelation of biodegradable poly(ω-caprolactone) and poly(ethylene glycol) multiblock copolymers in aqueous solutions, Journal of Controlled Release 73 (2001) 315-327.
Wilfred F.A. Den Dunnen et al., Long-term evaluation of nerve regeneration in a biodegradable nerve guide, Microsurgery 14:508-515 (1993).
Maurizio Penco et al., Multiblock copolymers based on segments of poly (D,L-lactic-glycolic acid) and Poly (ethylene glycol) or Poly (ω-caprolactone): A Comparison of Their Thermal Properties and Degradation Behavior, Journal of Applied Polymer Sciences, vol. 78, 1721-1728 (2000).
Daan J.A. Crommelin et al., Shifting paradigdms: biopharmaceuticals versus low molecular weight drugs, Int'l Journal of Pharmaceutics 266 (2003) 3-16.
T. Kissel et al., Parenteral protein delivery systems using biodegradable polyesters of ABA block structure, containing hydrophobic poly(lactide-co-glycolide) A blocks and hydrophilic poly(ethylene oxide) B blocks, Journal of Controlled Release 39 (1996) 315-326.
Lorenz Meinel et al., Stabilizing insulin-like growth factor-I in poly(D,L-lactide-co-glycolide) microspheres, Journal of Controlled Release 70 (2001) 193-202.

(Continued)

*Primary Examiner* — Brian Gulledge
(74) *Attorney, Agent, or Firm* — Hoffmann & Baron, LLP

(57) ABSTRACT

The invention is directed to biodegradable, thermoplastic, phase separated segmented multi-block copolymers. The copolymers of the present invention find use in various biomedical applications as well as in pharmaceutical applications. Provided is a composition for the controlled release of at least one biologically active polypeptide to a host, comprising the at least one biologically active polypeptide encapsulated in a matrix comprising at least one phase separated, thermoplastic multi-block copolymer, the copolymer being characterized in that (i) it comprises at least two hydrolysable segments chosen from prepolymer (A) and prepolymer (B), prepolymer (A) having a Tg lower than 37° C. and prepolymer (B) having a Tm of 40° C.-100° C. under physiological conditions; (ii) the segments being linked by a multifunctional chain-extender; (iii) the segments are randomly distributed over the polymer chain; and (iv) prepolymer (A) contains a segment that is derived from a water soluble polymer.

24 Claims, 8 Drawing Sheets

(56) References Cited

OTHER PUBLICATIONS

M. Malin et al., Biodegradable Lactone Copolymers. II. Hydrolytic Study of ω-Caprolactone and Lactide Copolymers, Journal of Applied Polymer Sicence, vol. 59, 1289-1298 (1996).

Xian Jun Loh et al., Controlled drug release from biodegradable thermoresponsive physical hydrogel nanofibers, Journal of Controlled Release 143 (2010) 175-182.

Ferdinand I. Broekema et al., In vitro analysis of polyurethane foam as a topical hemostatic agent, J. Majer Sci. Mater Med. (2011) 22:1081-1086.

L.H. Sperling, Nomenclature and Notational Problems in the Phase Separation Characteristics of Block copolymers, XP55027137A, 1996.

Copolymer, Wikipedia, XP55027143 (2012).

Y. Lemmouchi et al., Biodegradable polyesters for controlled release of trypanocidal drugs: in vitro and in vivo studies, Biomaterials 19 (1998) 1827-1837.

M. Hiljanen-Vainio et al., Biodegradable Lactone Copolymers. I. Characterization and Mechanical Behavior of ω-Caprolactone and Lactide Copolymers, Journal of Applied Polymer Science, vol. 59, 1281-1288 (1996).

* cited by examiner

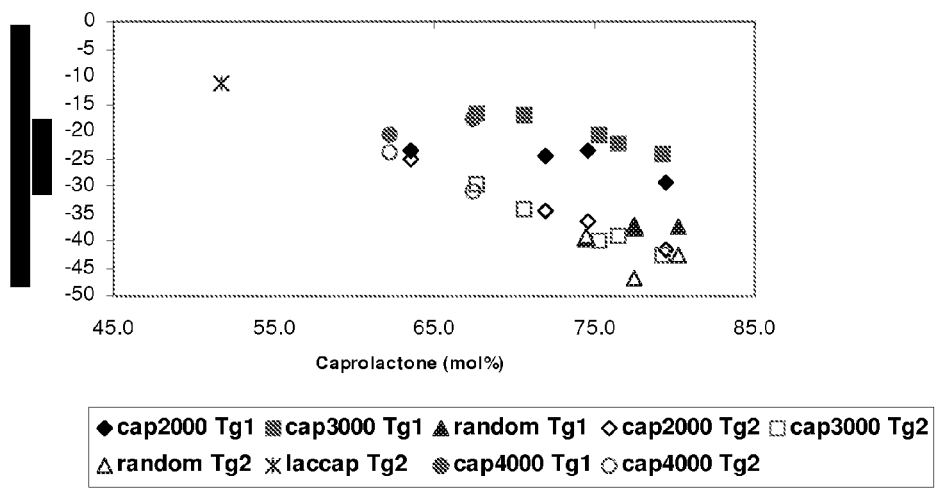
Figure 2: Glass transition temperature vs caprolactone content
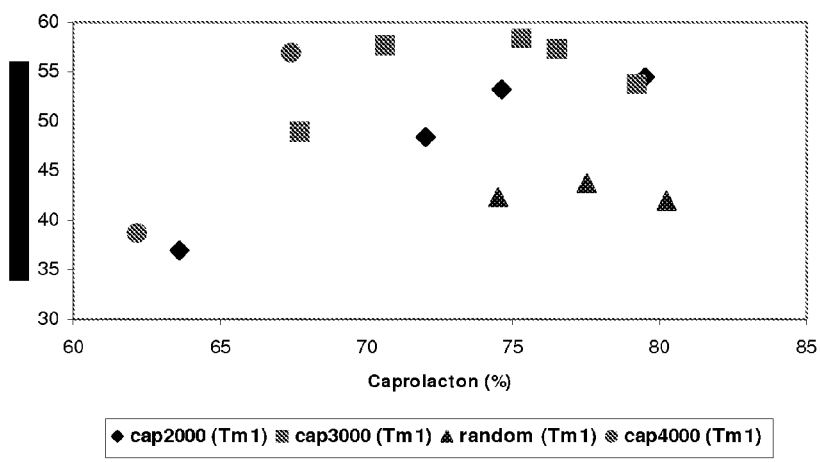
Figure 3: Melting temperature vs caprolactone content

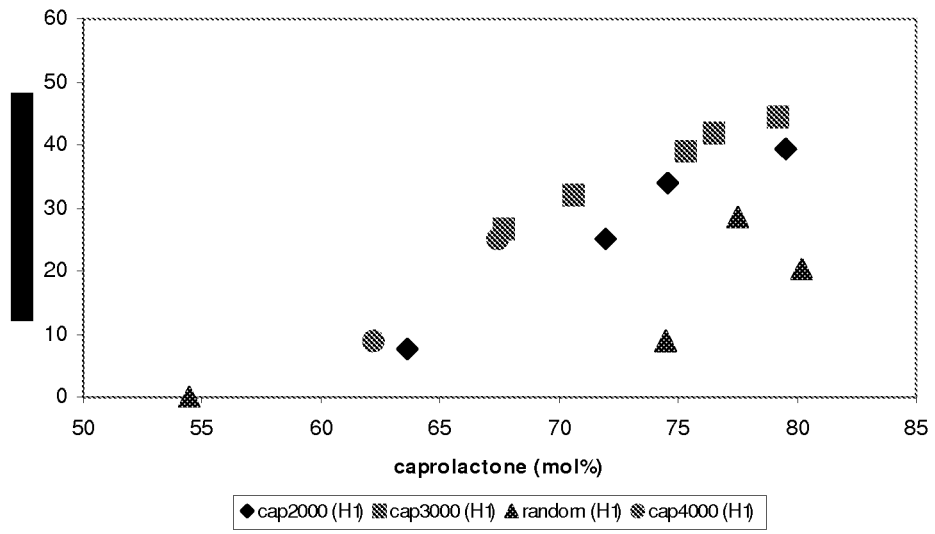
Figure 4: Melting enthalpy vs caprolactone content
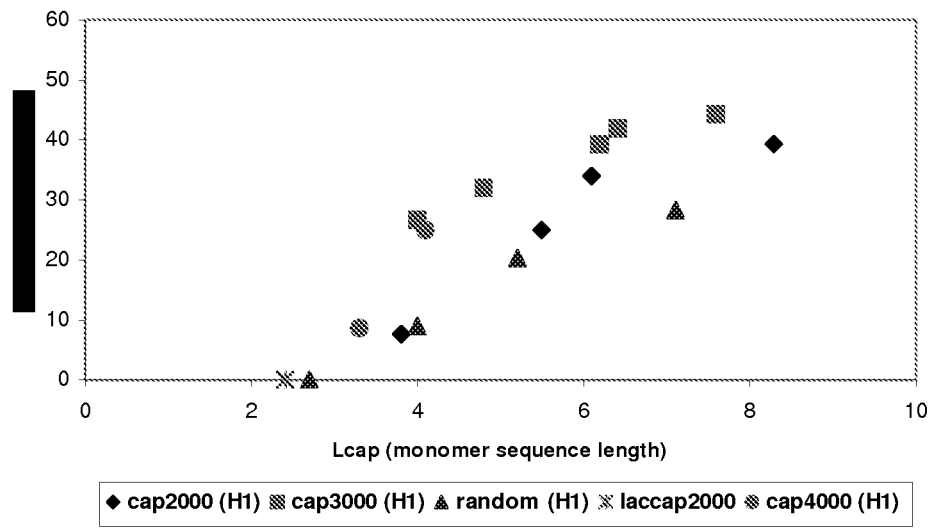
Figure 5: Melting enthalpy vs average caprolactone sequence length

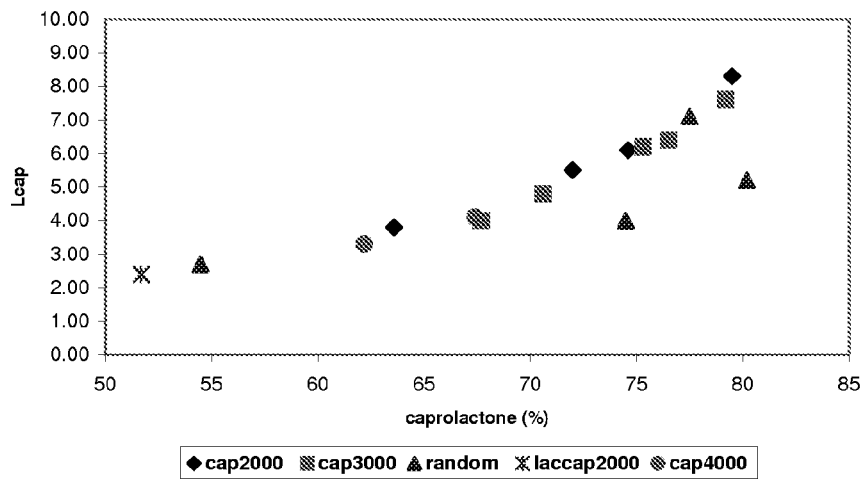
Figure 6: Average caprolactone sequence length vs caprolactone content
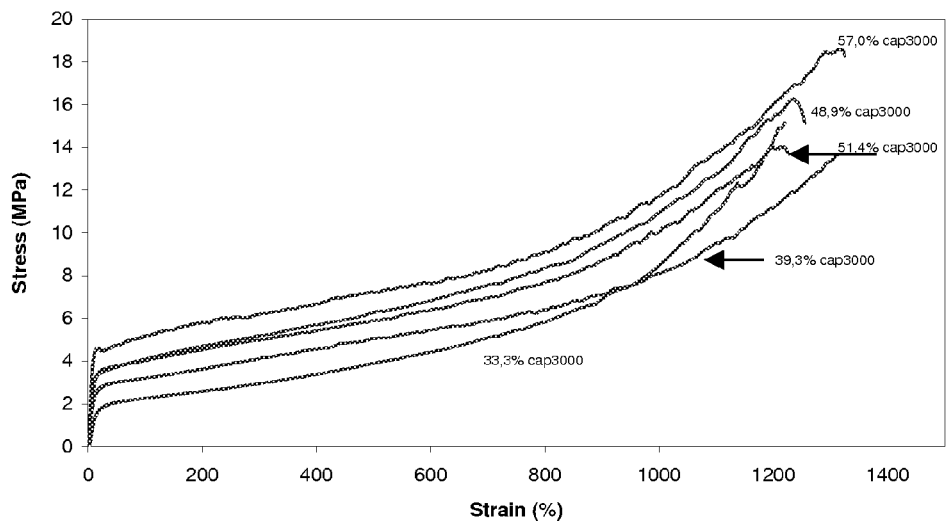
Figure 7: Stress vs strain of copolyesters with cap3000 pre-polymer

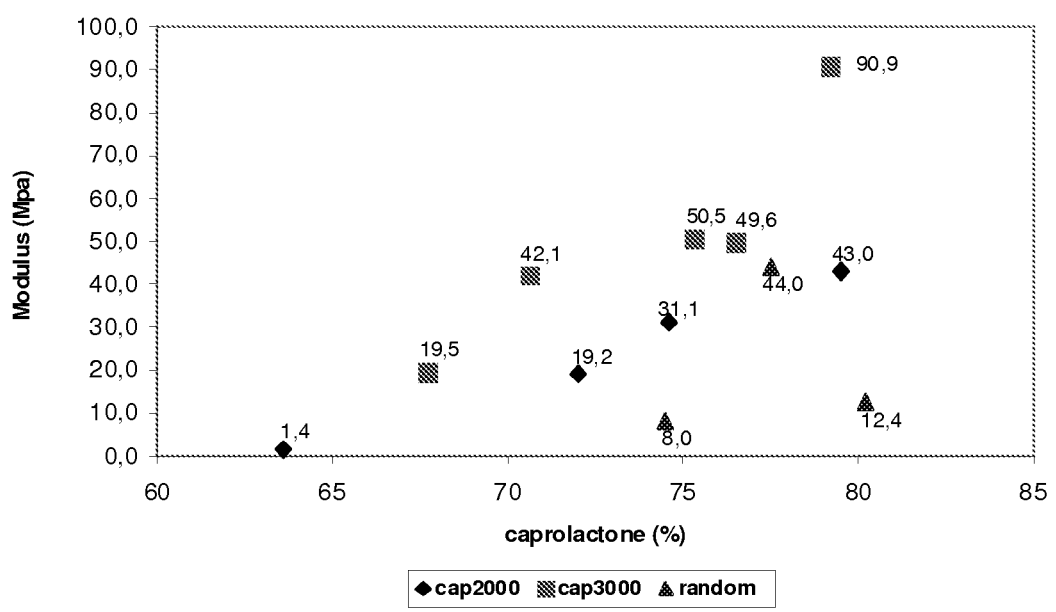
Figure 8: Modulus vs caprolactone content

Figure 9  Typical DSC thermograms of 50CLPEG15CL20-b-CL40 (A) and 50LAPEG15LA20-b-CL40 (B). Only reversing heat flow is shown.
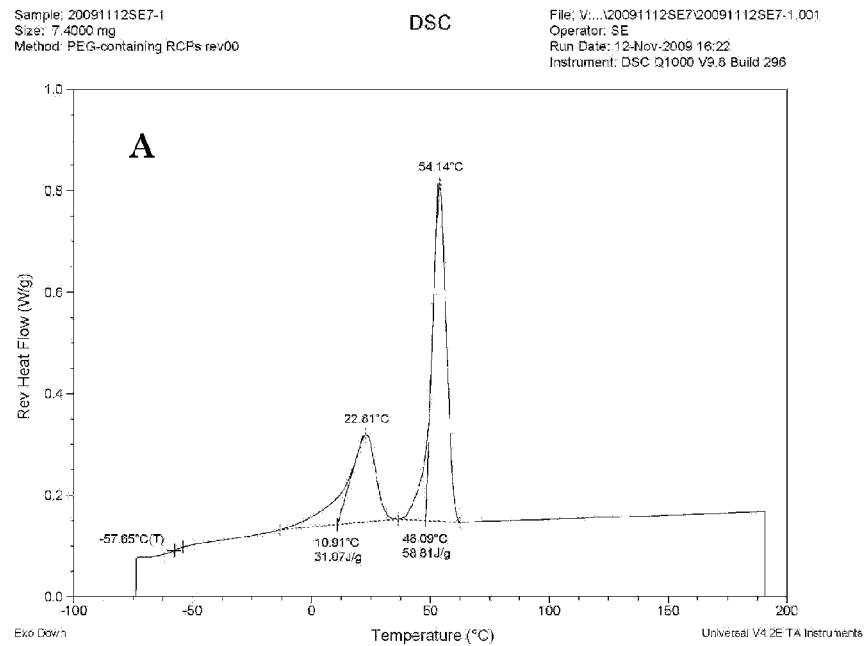
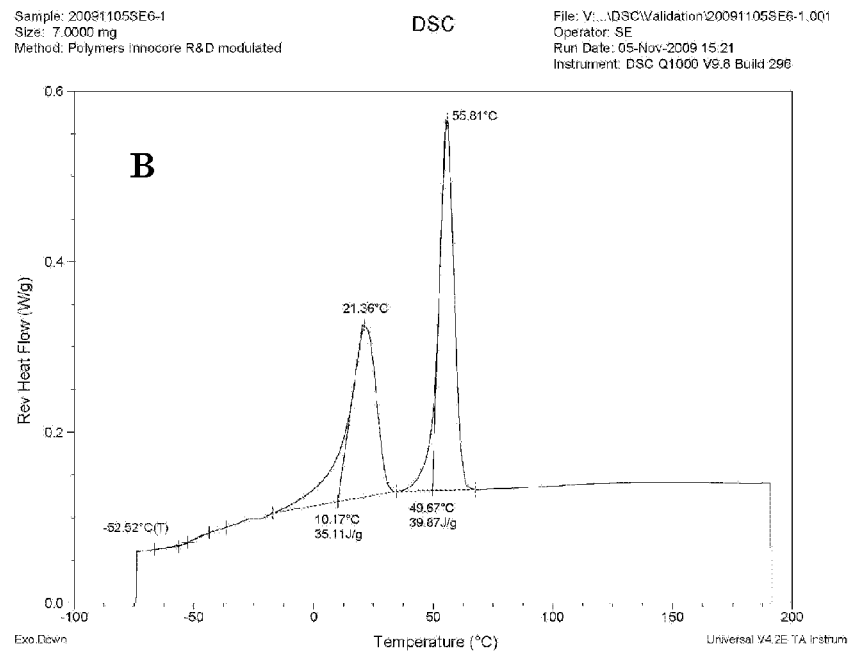

Figure 10  Lysozyme release from 30CLPEG15CL20-b-CL40, 50CLPEG15CL20-b-CL40 and 70CLPEG15CL20-b-CL40 multi-block copolymers.
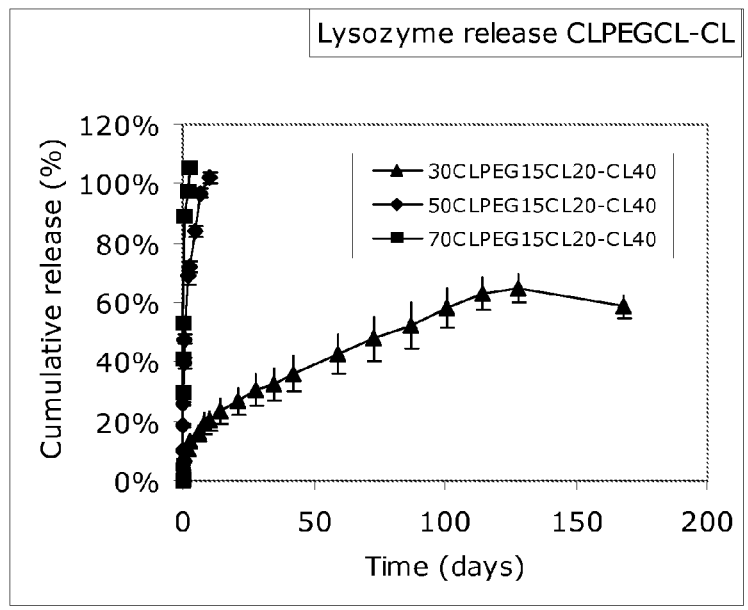
Figure 11  BSA release from 50CLPEG15CL20-b-CL40, 70CLPEG15CL20-b-CL40 and multi-block copolymers.
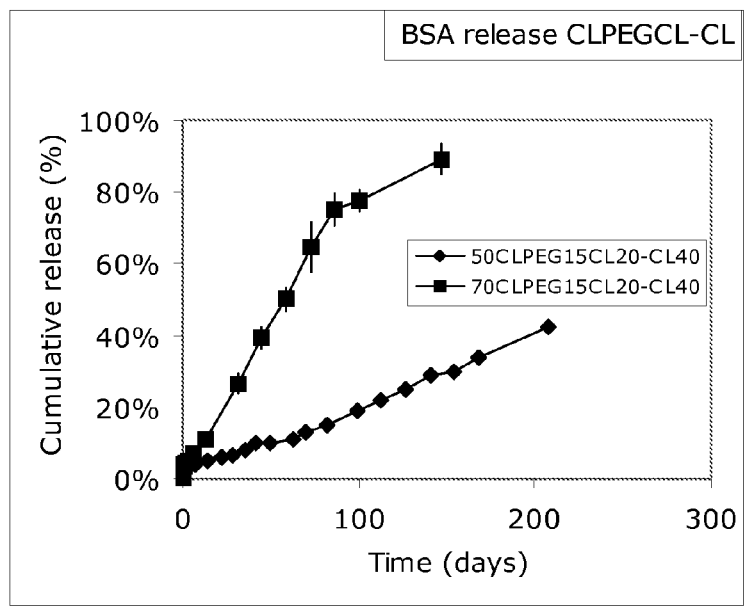

Figure 12: In vitro release of Lysozyme from PLGA and 30CLP10CL20-b-CL40 extrudates at 10 wt% Lysozyme loading in PBS, pH 7.4, at 37 °C.
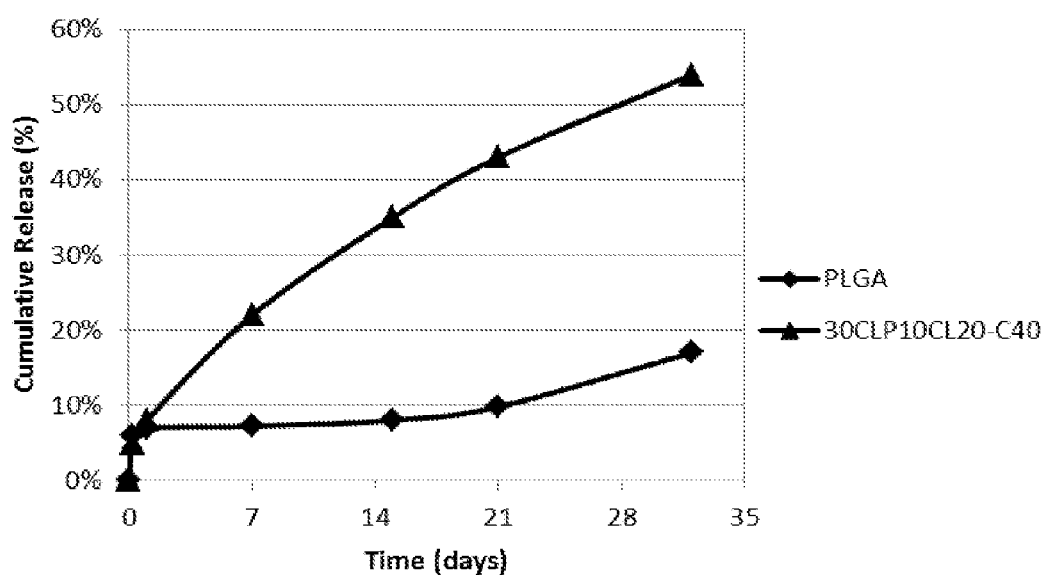

BIODEGRADABLE PHASE SEPARATED SEGMENTED MULTI BLOCK CO-POLYMERS AND RELEASE OF BIOLOGICALLY ACTIVE POLYPEPTIDES

This application is the U.S. National Phase of, and Applicants claim priority from, International Application Number PCT/NL2011/050502 filed Jul. 8, 2011 and U.S. Provisional Patent Application No. 61/362,710 filed Jul. 9, 2010, each of which are incorporated herein by reference.

BACKGROUND OF THE INVENTION

The invention is directed to biodegradable, thermoplastic, phase separated segmented multiblock copolymers, and the use thereof as delivery vehicle, in particular for biologically active agents such as proteins and peptides. The copolymers of the present invention find use in various biomedical as well as pharmaceutical applications.

Generally, thermoplastic phase separated co-polymers consist of a low glass transition temperature (Tg), flexible 'soft', amorphous, segment and a high Tm (semi)crystalline 'hard' segment which are incompatible or only partially compatible.

Examples of phase separated segmented/block copolymers are found e.g. in U.S. Pat. Nos. 6,255,408, 5,554,170, 5,066,772, 5,236,444, 5,133,739 and 4,429,080. These known materials are bioresorbable co-polyesters wherein the hard blocks are predominantly built of crystalline poly-glycolide and/or poly-lactide. Glycolide rich polyesters are especially suitable for fast resorbable biomedical articles such as mono- or multi filament sutures; L-lactide rich polyesters are used in more slowly resorbing medical applications, such as nerve guides, nerve graft and many other products. However, the high melting point of the poly-glycolide or poly-L-lactide rich blocks requires very high polymerisation and processing temperatures (about 200° C.), which may result in unwanted degradation behavior and/or trans-esterification. Furthermore, the poly-glycolide rich polyesters are unsuitable for applications for which a slow resorption is needed.

As an alternative to polyglycolide rich polyesters, poly-L-lactide rich copolyesters have been suggested as materials which have a higher resorption time and very good mechanical properties as a result of the crystalline segments. However, the use of a semi-crystalline random copolymer of L-lactide and ε-caprolactone (50/50) for bridging of peripheral nerve defects and of highly crystalline poly-L-lactide as bone plates have caused some severe problems in the past. Mild to severe foreign body reactions were observed after 2 to 3 years of implantation, respectively, due to the presence of long-lasting biomaterial fragments. (Den Dunnen et al. (Microsurgery 14 (1993) 508-515); Rozema et al. In: P. J. Doherty, R. L. Williams, D. F. Williams, eds. "Biomaterial-Tissue interfaces. Advances in biomaterials" 10 Amsterdam, Elsevier Science Publishers B.V. (1992) 349-355). It is an object of the present invention to provide a new biodegradable, thermoplastic, phase separated segmented multi-block copolymer, which does not suffer from the above-mentioned disadvantages and thus opens possibilities for new medical applications. A further object relates to the provision of a copolymer which is suitably used to encapsulate polypeptides.

DESCRIPTION OF THE INVENTION

The copolymer of the invention is composed of at least two different segments each having different physical characteristics, including degradation characteristics, and is characterized by good mechanical properties, in particular good tensile strength, elongation and elastic properties. Due to their phase separated morphology, the materials of the present invention are also suitable for constructing drug delivery matrices and drug eluting coatings, which may be used to enclose a certain therapeutic agent and to release the this agent at a desired time and/or location. As is described herein below, the material is of particular interest for the controlled release of a polypeptide, such as a biologically active polypeptide to a host.

It has been found that these properties can be obtained by a biodegradable, phase separated copolymer, comprising segments of a soft biodegradable prepolymer (A) having a Tg not more than 37° C.; and segments of a hard biodegradable prepolymer (B) having a phase transition temperature of 40-100° C., in which copolymer the segments are linked by a multifunctional chain-extender.

The term "phase-separated", as used herein, refers to a system, in particular a copolymer, built of two or more different prepolymers, of which at least two are incompatible with each other at temperatures of 40° C. or below (under physiological conditions such as in the human body). Thus the prepolymers do not form a homogeneous mixture when combined, neither when combined as a physical mixture of the prepolymers, nor when the prepolymers are combined in a single chemical species as "chemical mixture", viz. as copolymer.

The term "prepolymer" refers to the chemical units or building blocks making up the copolymer of the present invention. Each prepolymer may be obtained by polymerization of suitable monomers, which monomers thus are the building blocks of each prepolymer. The desired properties of the prepolymers and, by consequence, of the copolymer of the present invention, may be controlled by choosing a prepolymer of a suitable composition and molecular weight (in particular Mn), such that the required Tm or Tg is obtained.

The morphology of the polymer (or of the device made thereon is dependent on the environmental conditions: a differential scanning calorimetry (DSC) measurement may be performed under inert (dry) conditions and the results may be used to determine the dry materials' thermal properties. However, the morphology and properties at physiological conditions (i.e., in the body) and ambient conditions (room temperature) may be different. It is to be understood that the transition temperatures, Tg and Tm as used herein, refer to the corresponding values of a material when applied in vivo; viz. when at equilibrium with an atmosphere that is saturated with water vapor and at body temperature. This may be simulated in vitro by performing the DSC measurement after allowing the material to equilibrate with a water-saturated atmosphere (typically this may take several minutes to one hour). Upon application in vivo, however, the dry material's Tg and/or Tm will drop as a result of the absorption of water and this final Tg should be about body temperature or lower according to the present invention. The final Tm should be present at temperatures between 40-100° C.

For instance, a polymer that contains PEG in the soft segment can be crystalline under dry conditions at ambient temperature, while amorphous under wet conditions, giving a mixed Tg or two separated Tg's of the soft segment formed by amorphous softened PEG and the polyester/carbonate. The phase-separated quality of the copolymers of the present invention is reflected in the profile of the glass transition temperature (Tg) or melting temperature (Tm). Whereas a single prepolymer is usually characterized by a single phase transition (Tg or Tm), the phase-separated copolymers are characterized by at least two phase transitions, each of which is related to (but not necessarily identical to) the corresponding Tg or Tm values of the prepolymers which are comprised in the copolymer. Prepolymers which would form an (ideal) mixture or blend would result in a copolymer having a single Tg or Tm. The glass transition temperature, Tg, is determined by taking the midpoint of the specific heat jump, as may be measured e.g. by DSC. The melting temperature, Tm, is the peak maximum of the melting peak, as is schematically illustrated in FIG. 1, that shows the heat flow endotherm for a copolymer characterized by a Tg and a Tm. As defined herein, values of Tg and Tm of a certain prepolymer reflect the values as measured on the copolymer. In case of complete immiscibility of the prepolymers, the Tg of the copolymer is governed solely by the Tg of the amorphous, "soft" prepolymer. In most cases, however, the composition of the hard and the soft segments of the copolymer is not exactly the same as the composition of the prepolymers from which the copolymer is prepared. Part of the original hard segment forming prepolymer will mix with the soft prepolymer and thus become part of the soft phase. The Tg value of the soft segment is then different from that of the prepolymer used. The extent of miscibility (and therefore the deviation of Tg and/or Tm from those of the corresponding pre-polymers) is dependent on the prepolymer composition, ratio and segment length in the copolymer. In case a semi-crystalline prepolymer is used for building the hard segment, the amorphous part of this segment may also be immiscible with the other amorphous prepolymer segment, thus resulting in two different glass transition temperatures, both being more or less similar to the glass transition temperatures of their respective prepolymers. In case the soft segment is semi-crystalline (e.g. when polyethyleneglycol, PEG, is part of the pre-polymer), the polymer may consist of two crystalline phases: one as part of the soft segment and one in the hard segment. The low and high temperature phase transitions that characterize the phase separated copolymers of this invention are predominantly determined, by the contributions of the respective soft- and hard segments forming the biodegradable pre-polymers. On the one hand Tg and Tm of the final copolymer may be entirely determined by the corresponding values of the pre-polymers. On the other hand deviations from these "ideal" values may occur, as a result of partial phase mixing, which in practice is frequently observed.

The Tg of the copolymer segments generally lies between the value of the phase mixed copolymer and those of the separate prepolymers.

The multi-block copolymers of this invention have advantages over the block-copolymers known from the prior art, e.g. the block copolymers of structure ABA as mentioned in the examples of the introduction. Although polymer properties can be greatly improved by using block copolymers with blocks of different copolymers instead of homo- or random copolymers, they still have some disadvantages.

To obtain a minimum molecular weight of the copolymer, the sequences A and B must have a certain length. The blocks may independently behave as the individual homopolymers with similar composition. Properties of the ABA type copolymers can only be tuned by varying the composition of A and B blocks. Another disadvantage is that block copolymers must be prepared at relatively high temperatures (>100° C.) under inert conditions for complete conversion of all the monomers and to obtain sufficient molecular weight. The first disadvantage can be solved by using multiblock copolymers wherein the blocks or segments are much shorter and linked together by a chemical reaction. Properties such as degradation behaviour can be tuned in a much better way by choosing the proper combination of segment lengths, ratio and composition.

Furthermore, by the process of preparing ABA block copolymers (and derivatives thereof), there is always a possibility of transesterification, resulting in a certain extent of phase mixing. The multi-block copolymers of the present invention do not suffer from this disadvantage since they can be prepared by linking pre-polymers with previously determined monomer composition at rather low temperatures (<100° C.) thus avoiding transesterification and other side-reactions reactions, which may cause the generation of undesired degradation and other by-products. This means that the monomer sequence length of the copolymer is determined by the choice of building components and not so much by reaction time and temperature, as being usually applied for synthesis of random copolymers. An advantage of multi-block copolymers of this invention prepared by linking of pre-polymers using a multifunctional chain-extender is that pre-polymer segments may be randomly distributed in the copolymer by choosing all possible prepolymer ratios and segment lengths, thus offering much more possibilities of tuning the properties.

Known multiblock copolymers of two types of biodegradable prepolymers on the other hand, can only be made in an alternating pre-polymer sequence, resulting in a limited range of possible variables. (M. Penco, F. Bignotti, L. Sartore, S. D'Antone and A. D'Amore, J. Appl. Pol. Sci. Vol. 78, 1721-1728 (2000)).

It is further noticed that the random multiblock copolymers of the present invention provide many advantages that cannot be obtained with alternating multiblock copolymers.

Firstly, the random multiblock copolymers obtained by chain extension of A and B blocks have an unlimited A to B ratio. A:B can, for instance, be 10:90, but may as well be 90:10. In contrast, the ratio of the blocks in an alternating multiblock copolymer is limited to the ratio used in the chain extended polymer. For instance, in the case of chain extension of AB the A:B ratio in the multiblock copolymer is 50:50. The random nature of the multiblock copolymers of the present invention greatly increases the possible compositions of the material and thereby the control over its physical and chemical properties. This includes a better control of the swelling capacity in water, morphology (phase separation, amorphous/crystallinity) and polymer degradation.

Secondly, the synthesis method of the random multiblock copolymers of the present invention is much less laborious as compared to the synthesis of alternating multiblock copolymers. In alternating multiblock copolymers either segment A and B in case of AB diblocks, or segment A and C in case of ACA triblocks, have to be linked prior to chain extension (or a macro chain extender needs to be synthesised). In accordance with the present invention, separate A and B blocks are chain extended with e.g. a commercially available chain extender.

Another advantage of the copolymers of the present invention is that they may be based on multifunctional (aliphatic) chain-extenders. By choosing the type and amount of chain-extender the polymers properties can be affected (for instance, the chain-extender may act as a softener or it may affect the degree of phase separation). The total degree of freedom to obtain polymers with the desired properties is therefore increased compared to polymers of the prior art.

Biodegradable phase separated polyesters or polyester-carbonates of this invention are a promising group of biomaterials and can be used in various biomedical applications since they exhibit good mechanical, elastic and processing properties. Furthermore, they can be used in pharmaceutical applications, e.g. for drug delivery.

Biodegradable multi-block copolymers containing one hydrolysable polyester segment and one hydrophilic hydrolytically stable segment have been studied for their drug loading and release capacity e.g. poly(ε-caprolactone)-polyethyleneglycol (PEG) multiblock copolymers are described by Lee et al., J. Control. Release. 73 (2001) 315-27. The multi-block copolymers of the present invention are different from these known copolymers by the presence of at least two biodegradable segments instead of only one, therefore offering more possibilities of varying the degradation and drug release properties.

The mechanical and degradation properties of the multi block copolymers can be easily tuned by changing the type of monomers of the soft and hard segment forming pre-polymers and their chain length and ratio and by choosing the type and amount of chain-extender. Furthermore, the thermal properties are low enough for processing the polymer in the melt and high enough to be used as a biomedical device. The monomer ratio and distribution of the copolymer can be easily controlled by varying the polymerization conditions.

A crystalline hard segment is usually desired to obtain elastomeric and tough, non-sticky materials. A low Tg of the soft segment is usually necessary to obtain high elasticity. The phase separated character of the copolymers of the invention is very important for applications where good mechanical properties are required (such as porous scaffolds), since it enables that the hard segments may contribute to the mechanical strength, whereas the soft segments provide for the desired elastic properties. For drug delivery purposes, mechanical properties are less important, but the difference in physical properties of the two phases are essential. As mentioned previously, a prerequisite of the biomedical phase separated segmented co-polyester is that the melting point (i.e., phase transition temperature) of the polyester hard segment is larger than 40° C.: the phase separated morphology must also be present at body temperature and environment in order to retain the initial mechanical properties and structure of the device after implantation. An important class of segmented co-polyesters with such a good phase separation are those based on crystalline poly-ε-caprolactone hard segments. For example, a different approach to obtain semi-crystallinity in a lactide-ε-caprolactone copolymer that does not have long L-lactide sequences, is the use of a phase separated copolymer of DL-lactide and ε-caprolactone with a monomer ratio that results in crystallization of the caprolactone part of the copolymer. Since the rate of degradation of poly-ε-caprolactone is low, especially in the crystalline phase, it is also a good way to lower the degradation rate of the copolymer. In this way, biocompatible biomedical articles of ε-caprolactone rich copolymers can be applied in situations when a slow resorbing rate is desired without the use of a major L-lactide content. The low melting temperature of the crystalline phase (50-60° C.) makes this copolymer very easy to process.

This crystalline phase will have a melting point that is similar to or only a little lower than that of the high molecular weight homopolymer of ε-caprolactone (60-65° C.). To obtain a thermoplastic elastomer with a modulus that is not too high, the content of this hard phase can be rather low (either dispersed or in a co-continuous system with the rubber phase).

Generally, the desired phase separated morphology (reflected by one melting point and at least one low Tg value) may be obtained by varying the composition, e.g. by choosing the number average molecular weight, Mn, of the A and B prepolymers. It is also possible to influence the phase separated morphology by varying the A/B ratio.

Although random copolymers of lactide and ε-caprolactone with a crystallisable ε-caprolactone content have been prepared in the past, the phase separation is not as good as in the phase separated segmented/block co-polymers of this invention. This is proven by the much lower melting temperature of the crystalline ε-caprolactone segment, lower melting enthalpies (ΔH) and lower values of Tg (more amorphous ε-caprolactone present in the soft phase) of the random copolymers (see e.g. Hiljainen-Vainio et al., Lemmouchi et al., U.S. Pat. No. 4,643,734).

General Polymer Structures

The segmented multiblock copolymers of this invention consist of a soft segment which is preferably completely amorphous at body conditions, hydrolysable and with at least one phase transition being a Tg below 37° C. or preferably below 25° C. (as measured at body conditions). This segment will also be referred to herein as phase A. The copolymers of the present invention also contain a hard segment, consisting of a biodegradable crystalline or semi-crystalline polymer with a Tm equal to or larger than 40° C., but equal to or smaller than 100° C. (as measured at body i.e. physiological conditions) (phase B). The prepolymers A and B that form the "soft" and "hard" segments are linked by a multifunctional chain-extender. The "hard" and "soft" phases are incompatible or only partially compatible at body conditions. The multifunctional chain-extender is preferably an aliphatic molecule.

The resulting multiblock copolymers of the present invention preferably have a structure according to formulae (1):

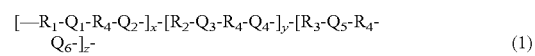

$$[-R_1-Q_1-R_4-Q_2-]_x-[R_2-Q_3-R_4-Q_4-]_y-[R_3-Q_5-R_4-Q_6-]_z- \quad (1)$$

wherein $R_1$ is part of phase (A) and may be amorphous polyester, amorphous polyetherester or amorphous polycarbonate; or an amorphous prepolymer that is obtained from combined ester, ether and/or carbonate groups. $R_1$ contains a water soluble polymer, which may result from the use of this compound as a polymerization initiator, the water soluble polymer being amorphous or crystalline at room temperature. However, the water soluble polymer thus introduced in $R_1$ will become amorphous at physiological conditions and therefore belongs to phase (A). In one embodiment, $R_1$ contain polyether groups, which may result from the use of these compounds as a polymerization initiator, the polyether being amorphous or crystalline at room temperature. However, the polyether thus introduced in $R_1$ will become amorphous at physiological conditions and therefore belongs to phase (A).

The initiator is generally a multifunctional molecule, which initiates the (ring-opening) polymerization. Suitable initiators are diols, like butanediol or PEG, and diacids.

$R_2$ mainly or entirely contributes to phase (B) and may be a crystalline or semi-crystalline polyester, polyetherester, polycarbonate or polyanhydride; or pre-polymers of combined ester, ether, anhydride and/or carbonate groups. It is possible that part of phase $R_2$ is amorphous, in which case this part of $R_2$ will contribute to phase (A).

$R_1$ and $R_2$ are not the same.

z is zero or a positive integer.

$R_3$ is a water soluble polymer, and may be present (z≠0) or not (z=0). $R_3$ will be part of the soft phase A under physiological conditions. Examples of water soluble polymers are polyethers such as polyethylene glycol (PEG), polytetramethyleneoxide (PTMO) and polypropyleneglycol (PPG); polyvinylalcohol (PVA) polyvinylpyrrolidone (PVP), polyvinylcarprolactam, poly(hydroxymethylmethacrylate) (poly-(HEMA)), polyphosphazenes, polyorthoesters, polyorthoesteramides or copolymers of the previous polymers, $R_4$ is an aliphatic $C_2$-$C_8$-alkylene group, optionally substituted by a $C_1$-$C_{10}$ alkylene, the aliphatic group being linear or cyclic. $R_4$ is preferably a butylene, —$(CH_2)_4$—, group. The $C_1$-$C_{10}$ alkylene side group may contain protected S, N, P or O moieties. x and y are both a positive integer.

Q1-Q6 are linking units obtained by the reaction of the prepolymers with the multifunctional chain-extender. Q1-Q6 may be independently selected from amine, urethane, amide, carbonate, ester and anhydride. The event that all linking groups Q are different being rare and usually not preferred.

Typically, one type of chain-extender may be used with three pre-polymers having the same end-groups resulting in a copolymer of formula (1) with six similar linking groups.

In case pre-polymers $R_1$ and $R_2$ are differently terminated, two types of groups Q will be present: e.g. Q1 and Q2 will be the same between two linked segments $R_1$, but Q1 and Q2 are different when $R_1$ and $R_2$ are linked. In copolymers of formula (2) and (3) the groups Q1 and Q2 are the same when two pre-polymers are present both terminated with the same end-group (which is usually hydroxyl), but are different when the pre-polymers are differently terminated (e.g. PEG which is diol terminated and a di-acid terminated 'tri-block' pre-polymer). The examples of formula (1), (2) and (3) show the result of the reaction with a difunctional chain-extender and difunctional prepolymers.

With reference to formula (1) the polyesters of the present invention may also be represented as multi-block or segmented copolymers having a random distribution of segments (ab)r, wherein 'a' corresponds to the segment $R_1$ that forms phase (A) and 'b' corresponds to the segment $R_2$ that forms phase (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the prepolymers. Preferably this is a difunctional chain-extender. In case z≠0, then the presentation of a random distribution of all the segments can be given by (abc)r were three different pre-polymers (one being a water soluble polymer, e.g. polyethyleneglycol) are randomly distributed in all possible ratio's.

The method to obtain a copolymer with a random distribution of a and b (and optionally c) is far more advantageous than when the segments are alternating in the copolymer such as in (ab)n with the ratio of prepolymers a and b being 1. The composition of the copolymer can then only be determined by adjusting the pre-polymer lengths. The a and b segment lengths in (ab)n alternating copolymers can be smaller than blocks in block-copolymers with structures ABA or AB.

The pre-polymers of which the a and b (and optionally c) segments are formed in (ab)r and (abc)r are linked by the difunctional chain-extender. This chain-extender is preferably a diisocyanate chain extender, but can also be a diacid or diol compound. In case the pre-polymers all contain hydroxyl end-groups, the linking units will be urethane groups. In case (one of) the prepolymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodiimide) forming ester linkages.

The term "Randomly segmented" copolymers refer to copolymers that have a random distribution (i.e. not alternating) of the segments a and b: (ab)r or a, b and c: (abc)r.

Polymerisation Method and Conditions:

Segmented multiblock co-polymers with structure (ab)r and (abc)r can be made by chain-extending a mixture of the pre-polymers, containing the hard- and the soft segment forming monomers of segments $R_1$ and $R_2$, and optionally $R_3$, in the desired ratio with an equivalent amount of a di-functional molecule, preferably an aliphatic molecule, more preferably a diisocyanate such as 1,4-butanediisocyanate (BDI). The segmented copolymers of structures (ab)r or (abc)r are preferably made in solution. The pre-polymer(s) are dissolved in an inert organic solvent and the chain-extender is added pure or in solution. The polymerisation temperature can be the same or even lower than the highest phase transition temperature of the pre-polymers. Coupling reactions with DCC are preferably carried out in solution. Two (or three) prepolymers that are all diol or diacid terminated are mixed in solution with a diacid or diol terminated chain-extender, respectively, after which DCC is added.

Polymerization takes place for a time long enough to obtain an intrinsic viscosity of the copolymer of preferably 0.2 dl/g or higher, such as 1 dug or higher. Solid state post polymerisation at room temperature may increase the molecular weight to an intrinsic viscosity up to 4 dl/g. The specific polymerisation time and temperatures for this bulk polymerisation are given in some examples below, but may be different for other pre-polymer combinations. The low polymerisation temperature and short polymerisation time will prevent from trans-esterification so that the phase separated morphology is obtained and the monomer distribution is the same as in the pre-polymers that build the copolymer. On the contrary, high molecular weight random copolymers have to be prepared at higher temperatures (>100° C.) and for a much longer time to obtain a full incorporation of all the monomers. During that time trans-esterification reactions will occur and a more random (which is less blocky) monomer distribution is obtained.

The segmented copolymers of structures (ab)r or (abc)r can also be made in the bulk at a temperature at which the pre-polymer mixture is a melt and which is at least 20° C. higher than the highest phase transition temperature of one of the pre-polymers.

The materials obtained by chain-extending in the bulk can also be produced in situ in an extruder.

If the chain-extender is a difunctional, aliphatic molecule and the pre-polymers are linear, a linear co-polymer is made; if one of the reactants (either the chain-extender or at least one of the pre-polymers) or both have more than two functional groups, branched structures may be obtained at sufficiently low conversion. Preferably, the chain-extender is an aliphatic di-isocyanate such as 1,4-butanediisocyanate.

The combination of hard- and soft phase forming pre-polymers is chosen in such a way to obtain a phase separated segmented or block co-polyester or polyester-carbonate with the desirable degradation, mechanical, physical and thermal properties. Since the two phases are chemically linked, the border of the phases is partly mixed and will result in good mechanical properties of the copolymer, even when the hard and soft segments are completely incompatible.

Pre-Polymers: Composition and Method of Preparation

The hydrolysable segment $R_1$ of formula (1) forming the soft phase A is obtained by reaction of pre-polymer A.

Pre-polymer (A) may e.g. be prepared by ring-opening polymerisation. Thus a prepolymer (A) may be a hydrolysable co-polymer prepared by ring-opening polymerisation initiated by a diol or di-acid compound, preferably having a random monomer distribution. The diol compound is preferably water soluble polymer, for example an aliphatic diol or a low molecular weight polyether. In one embodiment, it is polyethyleneglycol (PEG). The water soluble polymer is part of pre-polymer (A) by using it as an initiator and it can additionally be mixed with the pre-polymer A, thus forming an additional hydrophilic segment $R_3$ in formula (1). Pre-polymer (A) may be a hydrolysable polyester, polyetherester, polycarbonate, polyestercarbonate, polyanhydride or copolymers thereof, derived from cyclic monomers such as lactide (L, D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). To fulfill the requirement of a Tg below 37° C. of the soft segment, some of the above-mentioned monomers or combinations of monomers are more preferred than others. For example, pre-polymers (A) containing the monomers lactide and/or glycolide are preferably combined with any of the other mentioned cyclic co-monomers (ε-caprolactone, δ-valerolactone, trimethylenecarbonate, 1,4 dioxane-2-one and combinations thereof). This may by itself lower the Tg. Alternatively, the pre-polymer is initiated with a polyethylene glycol with sufficient molecular weight to lower the glass transition temperature of the soft segment.

Furthermore, pre-polymer A can be based on (mixtures of) condensation type of monomers such as hydroxyacids (e.g. lactic acid, glycolic acid, hydroxybutyric acid), diacids (e.g. glutaric, adipic or succinic acid, sebacic acid) and diols such as ethyleneglycol, diethyleneglycol, 1,4-butanediol or 1,6-hexanediol, forming ester and/or anhydride hydrolysable moieties.

The segment $R_2$ of formula (1), forming the hard phase (B) may be obtained by reaction of prepolymers (B) containing any hydrolysable, biocompatible polyester, polyetherester, polyestercarbonate, polyanhydride or copolymers thereof, and derived from both cyclic and non-cyclic monomers that are also used for building the pre-polymer (A), having a Tm between 40° C. and 100° C. Examples of the hard phase forming pre-polymers are polymers containing a crystallisable amount of ε-caprolactone, δ-valerolactone or para-dioxanone, hydroxyalkanoates or aliphatic anhydrides. Pre-polymers containing aromatic groups are generally not suitable for the hard phase forming pre-polymer, because they have a transition temperature that is too high (>100° C.). Furthermore, when the processing temperature is high, the solubility in common organic solvents is generally too low. Moreover, pre-polymers containing aromatic groups may give rise to undesired degradation products. This also holds for the chain-extenders used; although chain-extenders containing aromatic groups can be used, this is generally not preferred because of the undesired degradation products and the transition temperature that is too high. Therefore, aliphatic chain extenders are preferred.

Typically pre-polymer (B) has a Mn of larger than 1000, preferably larger than 2000, more preferably larger than 3000, which numbers particularly hold for the case where prepolymer (B) is poly-ε-caprolactone. In general Mn of pre-polymer (B) will be less than 10000. The content of prepolymer (B) in the copolymer is preferably 10-90 wt. %, more preferably 25-70 wt %, most preferably 30-50 wt. % (particularly for poly-ε-caprolactone).

The L/D ratio of the lactide used in amorphous poly-DL-lactide blocks or segments may be away from unity (other than 50/50). For instance, an L/D ratio between 85/15 and 15/85 gives an completely amorphous homo-polymer. Furthermore, it is known that an excess of one isomer (L or D) over the other increases the Tg of the poly-DL-lactide. A minor amount of any other of the above mentioned monomers that build the soft phase may also be present in the hard phase forming pre-polymer or block.

The pre-polymers will preferably be linear and random (co)polyesters, polyester-carbonates, polyetheresters, or polyanhydrides with reactive end-groups. These end-groups may be hydroxyl or carboxyl. It is preferred to have a dihydroxy terminated co-polymer, but hydroxy-carboxyl or dicarboxyl terminated polymers can also be used. In case the polymer has to be linear, it can be prepared with a di-functional component (diol) as a starter, but in case a three or higher functional polyol is used star shaped polyesters may be obtained. The diol can be an aliphatic diol or a low molecular weight polyether.

The pre-polymer synthesis by a ring-opening polymerisation is preferably carried out in the presence of a catalyst. A suitable catalyst is $Sn(Oct)_2$ with M/I=5000-30000. It is also possible to carry out the synthesis without a catalyst.

The conditions for preparing the polyesters, polycarbonates and polyanhydrides are those known in the art.

The copolymers of the present invention are generally linear. However, it is also possible to prepare the copolymers in a branched form. These non-linear copolymers of the present invention may be obtained by using a tri- (or more) functional chain extender, such as tri-isocyanate. Branched copolymers may show improved creep characteristics.

Pre-Polymer Length and Ratio of Pre-Polymers A and B in Segmented Co-Polyesters.

In case of a crystallisable hard segment, the length (number average molecular weight, Mn) of the pre-polymer must be large enough to be able to crystallise in the copolymer. E.g. poly-ε-caprolactone (PCL) hard segment forming pre-polymer is preferably larger than 1000, more preferably larger than 2000, most preferably larger than 3000. A larger PCL pre-polymer length results in a phase separated morphology at a lower hard segment content, as will be shown in the results. The pre-polymer ratio at which phase separation is observed is therefore dependent on the pre-polymer lengths. In general, the lengths of the pre-polymers that form the soft and hard segment within a copolymer must have a value at which a phase separated morphology is observed, the extent of phase separation (incompatibility) being favorable for the desired properties of the biomedical device.

The soft segment forming pre-polymer (A) has an Mn of larger than 500, preferably larger than 1000, more preferably larger than 2000. The length of the prepolymers must be chosen in such a way that they are as large as is necessary to obtain a good phase separated morphology and good mechanical and thermal properties of the resulting copolymer. The pre-polymer length must be low enough to be miscible with the chain-extender at the polymerisation temperature, typically this means that Mn is lower than 10000.

Generally, a hard segment content in the range of 10-90 wt. %, preferably of 25-60%, results in flexible, thermoplastic materials with good mechanical properties at the temperature of application (viz. about 37° C. for medical applications).

Polymer Properties and Applications

Very high molecular weights of the multiblock copolymers are not necessary to obtain good mechanical properties. With an intrinsic viscosity of the copolymer of about 0.8 dl/g the initial mechanical properties will be sufficient for the production of medical devices. For drug delivery applications, the intrinsic viscosity may even be lower, preferably between 0.2-2 dl/g. High intrinsic viscosities are undesirable, because the polymer will be difficult to process. Typically, the intrinsic viscosity is larger than 0.1 dl/g and less than 10 dl/g. Preferably, the intrinsic viscosities lie between 1-4 dl/g for medical implants.

The multiblock segmented copolymers can be formed into surgical articles using any known technique such as, for example, extrusion, molding, solvent casting and freeze drying. The latter technique is used to form porous materials. Porosity can be tuned by addition of co-solvents, non-solvents and/or leachables. Copolymers can be processed (either solid or porous) to films, sheets, tubes, membranes, meshes, fibers, plugs, coatings, microspheres and other articles. Products can be either solid, hollow or (micro)porous. A wide range of surgical articles can be manufactured for applications in for example wound care, skin recovery, nerve regeneration, vascular prostheses, drug delivery, meniscus reconstruction, tissue engineering, coating of surgical devices, ligament and tendon regeneration, dental and orthopedic repair. The copolymers can be used alone or can be blended and/or co-extruded with other absorbable or non-absorbable polymers.

Furthermore, they can be used in pharmaceutical applications, e.g. for drug delivery, e.g. in the form of microspheres or membranes.

As will be illustrated in the examples below, the materials of the present invention have improved properties, including thermal, mechanical, processing compared to copolymers described in the prior art.

Polypeptide Release

A further aspect of the invention relates to the encapsulation of at least one biologically active polypeptide (e.g. a biologically active protein or peptide) in the matrix of a phase separated, thermoplastic multi-block copolymer. It was found that a biodegradable copolymer of the invention is particularly suitable as delivery vehicle for a polypeptide, allowing for the controlled release of the polypeptide from the matrix into its environment, e.g. in the body of a subject.

Provided is for example a composition for the controlled release of at least one biologically active polypeptide to a host, comprising the at least one biologically active polypeptide encapsulated in a matrix comprising at least one phase separated, thermoplastic multi-block copolymer, the copolymer being characterized in that:

(i) it comprises at least two hydrolysable segments chosen from prepolymer (A) and prepolymer (B), prepolymer (A) having a Tg lower than 37° C. and prepolymer (B) having a Tm of 40° C.-100° C. under physiological conditions;

(ii) the segments being linked by a multifunctional chain-extender;

(iii) the segments are randomly distributed over the polymer chain;

(iv) prepolymer (A) contains a segment that is derived from a water soluble polymer.

The chain-extender can be a difunctional aliphatic chain-extender, preferably a diiosocyanate such as 1,4-butanediisocyanate.

As used herein, the term "multi-block" refers to the presence of several distinct segments in a polymer chain.

As used herein, the term "thermoplastic" refers to the non-crosslinked nature of the multi-block copolymer. When heated, a thermoplastic polymer becomes fluid and solidifies upon (re-)cooling.

As used herein, the term "hydrolysable" refers to the ability of reacting with water upon which the molecule is cleaved. Hydrolysable groups include ester, carbonate, phosphazene, amide and urethane groups. Under physiological conditions, only ester, carbonate and phosphazene groups react with water in a reasonable time scale.

As used herein, the term "multifunctional chain-extender" refers to the presence of at least two reactive groups on the chain-extender that allow for chain-extension, i.e. molecular weight build-up of prepolymers.

As used herein, the term "random" refers to a multi-block copolymer where the distinct segments are distributed randomly over the polymer chain.

As used herein, the term "water soluble polymer" is meant to refer to a polymer that has a good solubility in an aqueous medium, preferably water, under physiological conditions. This polymer, when copolymerized with more hydrophobic moieties, renders the resulting copolymer swellable in water. The water soluble polymer can be derived from a diol, a diamine or a diacid. The diol or diacid is suitably used to initiate the ring-opening polymerization of cyclic monomers. In one aspect, the composition comprises a copolymer as defined above wherein a water soluble polymer is present as an additional prepolymer. Preferably, the water soluble polymer is selected from the group consisting of polyethers such as polyethylene glycol (PEG), polytetramethyleneoxide (PTMO) and polypropyleneglycol (PPG); polyvinylalcohol (PVA) polyvinylpyrrolidone (PVP), polyvinylcarprolactam, poly(hydroxymethylmethacrylate) (poly-(HEMA)), polyphosphazenes, polyorthoesters, polyorthoesteramides or copolymers of the previous polymers. For example, the said water soluble polymeric segment is derived from PEG having a molecular weight of 150-5000 g/mol.

The copolymer in a composition of the invention can have an intrinsic viscosity of at least 0.1 dL/g, and preferably between 0.2 and 2 dL/g.

A polypeptide is a polymer of amino acids linked by peptide bonds. Short polypeptides are also referred to as peptides, whereas longer polypeptides are typically referred to as proteins. One convention is that those polypeptide chains that are short enough to be made synthetically from the constituent amino acids are called peptides rather than proteins. However, with the advent of better synthetic techniques, polypeptides as long as hundreds of amino acids can be made, including full proteins like ubiquitin.

Another convention places an informal dividing line at approximately 50 amino acids in length. This definition is somewhat arbitrary. Long polypeptides, such as the amyloid beta peptide linked to Alzheimer's disease, can be considered proteins; and small proteins, such as insulin, can be considered peptides. At any rate, the skilled person will appreciate that essentially any type of polypeptide can be encapsulated and subsequently released from a copolymer matrix. In one embodiment, a composition of the invention comprises a biologically active peptide or biologically active protein. Encapsulated polypeptides preferably contain only natural amino acids, although non-natural amino acids (i.e., compounds that do not occur in nature but that can be incorporated into a polypeptide chain) and/or amino acid analogues as are known in the art may alternatively be employed. Also, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification (e.g., alpha amidation), etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide.

As used herein, a "biologically active polypeptide" is intended to be broadly interpreted as any peptide or protein capable of eliciting a response in a biological system such as, for example, living cell(s), tissue(s), organ(s), and being(s). Biologically active polypeptides can include natural and/or synthetic polypeptides. Thus, a biologically active polypeptide is intended to be inclusive of any substance intended for use in the diagnosis, cure, mitigation, treatment, or prevention of disease or in the enhancement of desirable physical or mental development and conditions in a subject.

The biologically active peptide or biologically active protein is preferably selected from the group consisting of protein/peptide drugs, enzymes, receptor ligands, neurotransmitters, inhibitory peptides, regulatory peptides, activator peptides, cytokines, growth factors, monoclonal antibodies, anti-tumor peptides, antibiotics, antigens, vaccines and hormones. Exemplary polypeptides to be encapsulated are mentioned in U.S. Pat. No. 5,980,948 and D. J. A. Crommelin et al. Int. J. Pharm 266 (2003) 3-16. Of course, it is also envisaged to encapsulate two or more distinct (biologically active) polypeptides.

The size of the polypeptide(s) can vary. In one embodiment, the polypeptide has a molecular weight of less than 10,000. It was found that polypeptides of such size are particularly suitable to be encapsulated in the matrix of a copolymer comprising PEG as a segment of prepolymer (A) and/or as an additional prepolymer, said PEG having a molecular weight of from about 200 to about 3000, like 400 to about 3000 or 200 to about 1500, 600 to about 1500, preferably from about 600 to about 1000. Alternatively, or in addition, said PEG is present in an amount of from about 5% w/w to about 60% w/w, preferably of from about 5% w/w to about 40% w/w.

In another embodiment, said polypeptide is a biologically active protein having a molecular weight is 10,000 or more. These larger polypeptides are preferably encapsulated in the matrix of a copolymer which contains PEG, as a segment of prepolymer (A) and/or as an additional prepolymer, and wherein said PEG has a molecular weight of from about 600 to about 5000 and/or wherein said PEG is present in an amount of from about 5% w/w to about 70% w/w, more preferably of from about 10% w/w to about 50% w/w. Preferred PEGs for use in combination with larger polypeptides of 10,000 or more are those having a molecular weight of from about 600 to about 3000, like 1000 to about 3000.

A composition of the invention can have any desirable appearance or shape. In one embodiment, the matrix is processed in the form of a microsphere, microparticle, implant, coating, gel, film, foil, sheet, rod or membrane. Processing may involve extrusion or injection moulding. In view of the thermal susceptibility of the encapsulated polypeptide(s), it is preferred to that high processing temperatures (e.g. above 100°) are avoided. It was surprisingly found that a copolymer of the invention allows for processing at a relatively low temperature. Accordingly, processing e.g. by extrusion or injection moulding is advantageously performed at a temperature from about 20° C. to 80° C., preferably between about 30° C. to 60° C.

One specific aspect relates to a composition in the form of a coating. The coating may be applied as a drug-eluting coating e.g. on a medical implant, such as a vascular or urinary stent, an orthopaedic prosthesis or an ocular implant. Another specific aspect relates to a composition in the form of microspheres, preferably monodisperse microspheres. Methods for preparing (monodisperse) microspheres are known in the art. For example, WO 2005/115599 discloses a device for generating microspheres from a fluid, method of injecting at least one first fluid into a second fluid, and an injection plate. Still a further aspect relates to a composition in the form of an implant, preferably an injectable implant.

Also provided is a method for delivering a biologically active polypeptide of interest to a subject in need thereof, comprising administering an effective dose of a composition according to the invention to said subject. The subject is typically a mammal, preferably a human being. However, veterinary use of the present invention is also encompassed. The method can have a therapeutic, prophylactic, and/or cosmetic purpose. Any suitable mode of administration can be selected, depending on the circumstances. For example, administering may comprise the parenteral, intra-arterial, intra-articular, intra-venal, intra-ocular, epidural, intrathecal, intra-muscular or subcutaneous administration of a composition. In one embodiment, the invention provides a method for delivering a biologically active polypeptide of interest to a subject in need thereof, comprising administering an effective dose of a composition according to the invention to said subject, wherein the composition is in the form of microspheres, an injectable implant or an in situ forming gel and wherein the composition is administered intra-ocularly, intramuscularly or subcutaneously.

BRIEF DESCRIPTION OF THE DRAWINGS

FIG. 2 shows the relation between the glass transition temperature (Tg1 of first DSC run, Tg2 of second DSC run) and the $\epsilon$-caprolactone content of co-polyesters with different PCL pre-polymer lengths and of random copolymers of DL-Lactide and $\epsilon$-caprolactone: ♦ (closed diamonds): Tg1 of co-polyester with PCL2000 pre-polymer; ◊ (open diamond): Tg2 of co-polyester with PCL2000 pre-polymer; ■ (closed square): Tg1 of co-polyester with PCL3000 pre-polymer; □ (open square): Tg2 of co-polyester with PCL3000 pre-polymer; ● (closed circle): Tg1 of co-polyester with PCL4000 pre-polymer; ○ (open circle): Tg2 of co-polyester with PCL4000 pre-polymer; ▲ (closed triangle): Tg1 of random co-polyester; Δ (open triangle): Tg2 of random co-polyester; *: Tg2 of co-polyester with lactide-$\epsilon$-caprolactone pre-polymer with Mn=2000.

FIG. 3 shows the relation between the melting temperature (peak maximum, Tm) of the first DSC run and the $\epsilon$-caprolactone content of co-polyesters with different PCL pre-polymer lengths and of random copolymers of DL-Lactide and $\epsilon$-caprolactone: ♦ (closed diamonds): Tm1 of co-polyester with PCL2000 pre-polymer; ■ (closed square): Tm1 of co-polyester with PCL3000 pre-polymer; ▲ (closed triangle): Tm1 of random co-polyester; ● (closed circle): Tm1 of co-polyester with PCL4000 pre-polymer.

FIG. 4 shows the relation between the melting enthalpy (ΔH) of the first DSC run and the $\epsilon$-caprolactone content of co-polyesters with different PCL pre-polymer lengths and of random copolymers of DL-Lactide and $\epsilon$-caprolactone: ♦ (closed diamonds): ΔH1 of co-polyester with PCL2000 pre-polymer; ■ (closed square): ΔH1 of co-polyester with PCL3000 pre-polymer; ▲ (closed triangle): ΔH1 of random co-polyester; ● (closed circle): ΔH1 of co-polyester with PCL4000 pre-polymer.

FIG. 5 shows the relation between the melting enthalpy (ΔH) of the first DSC run and the average caprolactone sequence length, $\overline{L}_{Cap}$, of co-polyesters with different PCL pre-polymer lengths and of random copolymers of DL-Lactide and $\epsilon$-caprolactone: ♦ (closed diamonds): ΔH1 of co-polyester with PCL2000 pre-polymer; ■ (closed square):

Figure 1:
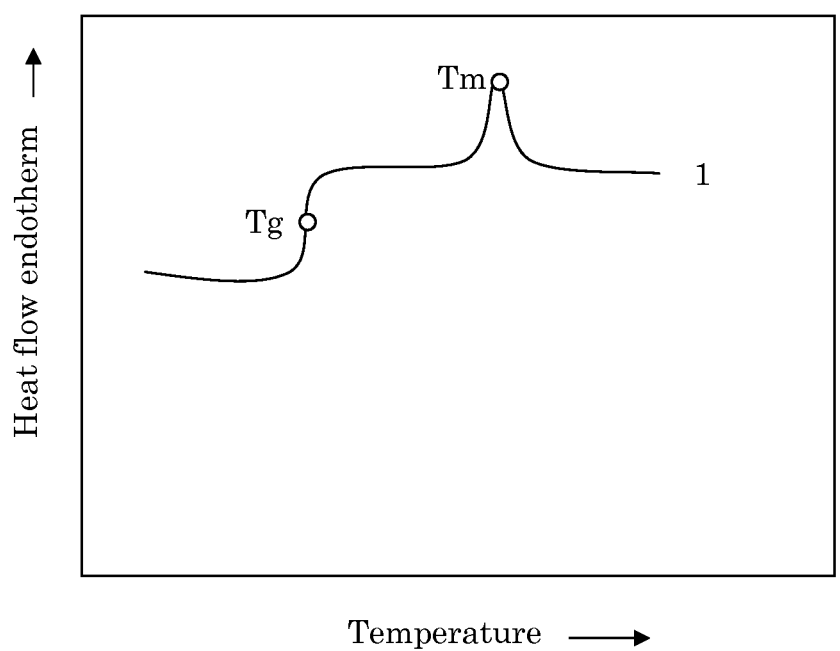
FIG. 1 shows the heat flow endotherms of phase separated copolymers, being characterised by a Tg and a Tm of a copolymer.

ΔH1 of co-polyester with PCL3000 pre-polymer; ▲ (closed triangle): ΔH1 of random co-polyester; ● (closed circle): ΔH1 of co-polyester with PCL4000 pre-polymer; *: ΔH1 of co-polyester with lactide-ε-caprolactone pre-polymer with Mn=2000.

FIG. 6 shows the relation between the average caprolactone sequence length, $\overline{L}_{Cap}$ and ε-caprolactone content of co-polyesters with different PCL pre-polymer lengths and of random copolymers of DL-Lactide and ε-caprolactone: ♦ (closed diamonds): $\overline{L}_{Cap}$ of co-polyester with PCL2000 pre-polymer; ■ (closed square): $\overline{L}_{Cap}$ of co-polyester with PCL3000 pre-polymer; ● (closed circle): $\overline{L}_{Cap}$ of co-polyester with PCL4000 pre-polymer; ▲ (closed triangle): $\overline{L}_{Cap}$ of random co-polyester. (closed circle): *: $\overline{L}_{Cap}$ of co-polyester with lactide-ε-caprolactone pre-polymer with Mn=2000.

FIG. 7 shows the stress-strain behavior of the segmented co-polyesters with the PCL3000 pre-polymer with different PCL3000 content.

FIG. 8 shows the relation between the elastic modulus (E) and the ε-caprolactone content of co-polyesters with different PCL pre-polymer lengths and of random copolymers of DL-Lactide and ε-caprolactone: ♦ (closed diamonds): E of co-polyester with PCL2000 pre-polymer; ■ (closed square): E of co-polyester with PCL3000 pre-polymer; ▲ (closed triangle): E of random co-polyester.

FIG. 9 shows typical reversing heat flow signals of the DSC thermograms obtained for 50CLPEGCL15CL20-b-CL40 (FIG. 9A) and 50CLPEGCL15CL20-b-CL40 (FIG. 9B).

FIG. 10 shows the release of lysozyme from 30CLPEGCL15CL20-b-CL40 (▲closed triangle), 50CLPEGCL15CL20-b-CL40 (♦ closed diamonds) and 70CLPEGCL15CL20-b-CL40 (■ closed squares) multi-block copolymers.

FIG. 11 shows the release of bovine serum albumin from 50CLPEGCL15CL20-b-CL40 (♦ closed diamonds) and 70CLPEGCL15CL20-b-CL40 (■ closed squares) multi-block copolymers.

FIG. 12 shows the in vitro release of lysozyme from 30CLP10CL20-b-CL40 extrudates at 10 wt % Lysozyme loading in PBS, pH 7.4, at 37° C.

EXAMPLES

Analysis Methods:

The following analysis methods were used in all examples, unless indicated otherwise.

The intrinsic viscosity was measured in chloroform at 25° C. using an Ubbelohde viscometer (according to ISO standard 1628-1).

Molecular weights were determined by Gel Permeation Chromatography at 30° C. using a Spectra Physics instrument equipped with 2 PL-Mixed-C columns (Polymer Labs), operating with tetrahydrofuran as eluent and with a Shodex RI-71 refractometer. Samples were dissolved in THF (1 mg ml$^{-1}$), the injection volume was 1000 and the flow rate 1 ml min$^{-1}$ Calibration curves were obtained by polystyrene standards.

Pre-polymer and copolymer composition, monomer distribution (average sequence length, $\overline{L}_{Lac}$ and $\overline{L}_{Cap}$) were determined using $^1$H-NMR at 300 MHz in solutions in deuterated chloroform.

Thermal properties were determined under a nitrogen atmosphere using a Perkin-Elmer DSC-7, 5-10 mg samples being heated at a rate of 10° C. per minute, cooled down at a rate of 10° C. per minute, hold for 1 minute at −90° C. and heated again at a rate of 10° C. per minute. Tg and Tm were determined from the resulting DSC curves.

The stress strain behavior was determined on an Instron 4301 tensile tester. Thin films (0.25 mm) were measured at room temperature at a cross-head speed of 10 mm/minute. The ultimate tensile strength, the stress at 250% strain, the elongation at break and the initial modulus were determined from these measurements.

Films were prepared by evaporating a solution of the co-polyester in chloroform in a petri-dish during 7 days at room temperature.

Polymer properties are given in Tables 1-5.

The following notation is used to indicate the composition of the copolymers: e.g. the columns cap2000 and dl-lac/cap2000 in Table 1 give the ratio of the two pre-polymers (% w/w) (cap2000 is PCL pre-polymer with Mn=2000; dl-lac/cap2000 is DL-Lactide-ε-caprolactone pre-polymer with Mn=2000). The first column gives the molar co-monomer composition of the resulting copolymer: e.g. P(CL-DLLA) 80-20 contains 80 mol % ε-caprolactone (the total amount of ε-caprolactone in the two pre-polymers) and 20 mol % of DL-lactide.

Examples Prepolymers

Example 1

DL-Lactide-ε-caprolactone Prepolymer (Mn=2000)

32.82 grams (0.231 mol) DL-Lactide (Purac, the Netherlands) was introduced into a three-necked bottle under nitrogen atmosphere and was dried in vacuum at 45° C. for at least 8 hours. ε-Caprolactone (Acros, Belgium) is dried over CaH$_2$ and distilled under reduced pressure in a nitrogen atmosphere. 26.32 grams (0.231 mol) ε-caprolactone was added under a nitrogen flow. 2.68 grams (29.7 mmol) of 1,4-butanediol (Acros, distilled from 4 Å molecular sieves after drying for 8 hours) was added. 24.8 mg stannous octoate (Sigma Corp) was added (M/I=8000). The mixture was magnetically stirred and reacted at 130° C. during 162 hours. $^1$H-NMR showed complete monomer conversion. The lactide:ε-caprolactone ratio in the pre-polymer was 48.4:51.6 (calculated by $^1$H-NMR). The calculated molecular weight (Mn) was 2080 and was confirmed by end-group analysis with $^1$H-NMR.

Example 2

ε-Caprolactone Prepolymer (Mn=2000)

193.98 grams (1.70 mol) ε-Caprolactone (see example 1 for purification) was introduced into a three-necked bottle under nitrogen atmosphere. 8.74 grams (97.0 mmol) of 1,4-butanediol (see example 1 for purification) was added. 78.7 mg stannous octoate (Sigma Corp) was added (M/I=9130). The mixture was magnetically stirred and reacted at 130° C. during 160 hours. $^1$H-NMR showed complete monomer conversion. The calculated molecular weight (Mn) was 2090 and was confirmed by end-group analysis with $^1$H-NMR Example 3

ε-Caprolactone Prepolymer (Mn=3000)

A pre-polymer with Mn=3000 was prepared in the same way as described in example 2. The calculated molecular weight (Mn) was 3160 and was confirmed by end-group analysis with $^1$H-NMR

Example 4

General Polymerisation Method of Segmented Co-Polyesters with Randomly Distributed Segments: P(CL-DLLA)

The PCL pre-polymer (2000, 3000 or 4000) and DL-lactide-ε-caprolactone pre-polymer are pre-heated until 70° C. until they become more liquid. The appropriate amounts of both pre-polymers are weighted into a glass ampoule supplied with nitrogen inlet and a mechanical stirrer. 1 equivalent of 1,4-butanediisocyanate (Bayer, distilled at reduced pressure) is added. The contents of the ampoule are quickly heated to 65° C. and then stirred mechanically for 15 minutes. As the mixture becomes viscous, the temperature is increased to 80° C. Stirring is stopped when the mixture becomes too viscous (between ½-1½ hour) and the heating is continued for a maximum of 24 hours.

De ampoule is cooled to room temperature and post-polymerisation continues for 48 hrs. Then, the contents are isolated by dissolving the polymer in chloroform. The solution is filtered and poured into a petri-dish. The solvent is evaporated and after that the polymer film is dried in a vacuum oven at 40° C.

The polymer is stored in a sealed package at room temperature for at least 1 week before characterization takes place (thermal and mechanical properties and intrinsic viscosity). Polymer composition (average sequence length, $\overline{L}_{Lac}$ and $\overline{L}_{Cap}$) is determined by $^1$H-NMR.

Example 5

Synthesis of Random Co-Polyesters

Random copolymers were synthesized by a ring-opening polymerization in the bulk initiated by stannous octoate. DL-Lactide (Purac, the Netherlands) and ε-Caprolactone (Acros, Belgium; dried over $CaH_2$ and distilled under reduced pressure in a nitrogen atmosphere) were charged into a clean, dry glass ampoule with nitrogen inlet. Stannous octoate was added (see Table 3) and the ampoule was placed in an oil bath at 120° C. The contents were kept under nitrogen atmosphere. The ampoules were heated for 5 days and were then cooled to room temperature. A sample of the polymer was taken for NMR measurements. The polymers were dissolved in chloroform and precipitated in ethanol (96%). Films for thermal and mechanical analysis were made from the purified copolymers. Intrinsic viscosities were measured from the purified copolymers.

Example 6

Preparation of Nerve Guides

Copolymers prepared according to the method in Example 4 with various ε-caprolactone/lactide ratios and with both PCL2000 and PCL3000 pre-polymers have been used for preparation of nerve guides. To this end, for each copolymer a polymer solution in chloroform was dip-coated on mandrels with various diameters. After dipping, the mandrel was placed horizontally and the solvent was allowed to evaporate during 5 minutes while rotating. This procedure was repeated until the desired wall thickness was obtained. The mandrel with the copolymer layer was placed first in ethanol and after that in distilled water. The tubes were removed from the mandrel and were cut into the appropriate lengths. They were placed in ethanol, followed by vacuum drying at 40° C. in order to remove monomer- and low molecular weight residues and organic solvents.

Example 7

Preparation of Microspheres

A copolymer (1 gram) prepared according to the method in Example 4 containing 39.3% (w/w) of PCL3000 prepolymer is dissolved in 50 ml of dichloromethane. A 3% polyvinylalcohol (PVA Mw=22.000) solution in 800 ml water is made. The solutions are filtered. The PVA solution is stirred at a rate of 200-800 rpm during the whole process. The polymer solution is added to the PVA solution. The solutions are stirred during 1.5 hours while evaporating the dichloromethane at reduced pressure. The stirring is stopped and the microspheres are collected from the aqueous phase, after which they are washed several times with water. Finally, the microspheres are dried by vacuum or freeze-drying. According to this method, hollow microspheres with solid outer layer ($d_{50}$~25 μm) can be obtained. By slight modification of the process, also solid and porous particles and particles with a smaller or larger size can be prepared.

TABLE 1

Properties of segmented co-polyesters with PCL 2000 pre-polymer

| P(CL-DLLA) (mol %) | Composition (% w/w) | | [η] | $\overline{L}_{Cap}$ | $\overline{L}_{Lac}$ | $Tg_1$ (° C.) | $Tg_2$ (° C.) | $Tm_1$ (° C.) | $Tm_2$ (° C.) | $\Delta H_1$ (J/g) | $\Delta H_2$ (J/g) |
|---|---|---|---|---|---|---|---|---|---|---|---|
| | Cap2000 | dl-lac/cap 2000 | | | | | | | | | |
| 63.6-36.4 | 23.4 | 76.6 | 3.62 | 3.8 | 4.3 | −23.6 | −25.2 | 37.0 | — | 7.6 | — |
| 72.0-28.0 | 41.0 | 59.0 | 2.25 | 5.5 | 4.3 | −24.4 | −34.5 | 48.4 | — | 25.0 | — |
| 74.6-25.4 | 46.6 | 53.4 | 1.19 | 6.1 | 4.2 | −23.7 | −36.6 | 53.3 | 41.7 | 34.3 | 1.9 |
| 79.5-20.5 | 56.8 | 43.2 | 1.30 | 8.3 | 4.3 | −29.5 | −41.7 | 54.4 | 38.7 | 39.5 | 20.7 |

TABLE 2

Properties of segmented co-polyesters with PCL 3000 pre-polymer

| P(CL-DLLA) (mol %) | composition (% w/w) | | [η] | $\overline{L}_{Cap}$ | $\overline{L}_{Lac}$ | $Tg_1$ (° C.) | $Tg_2$ (° C.) | $Tm_1$ (° C.) | $Tm_2$ (° C.) | $\Delta H_1$ (J/g) | $\Delta H_2$ (J/g) |
|---|---|---|---|---|---|---|---|---|---|---|---|
| | Cap3000 | dl-lac/cap 2000 | | | | | | | | | |
| 67.7-32.3 | 33.3 | 66.7 | 1.99 | 4.0 | 3.8 | −16.8 | −29.6 | 49.0 | — | 26.7 | — |
| 70.6-29.4 | 39.3 | 60.7 | 1.27 | 4.8 | 4.0 | −17.1 | −34.3 | 57.7 | 45.4 | 32.0 | 1.82 |

TABLE 2-continued

Properties of segmented co-polyesters with PCL 3000 pre-polymer

| P(CL-DLLA) (mol %) | composition (% w/w) Cap3000 | dl-lac/cap 2000 | [η] | $\bar{L}_{Cap}$ | $\bar{L}_{Lac}$ | $Tg_1$ (°C.) | $Tg_2$ (°C.) | $Tm_1$ (°C.) | $Tm_2$ (°C.) | $\Delta H_1$ (J/g) | $\Delta H_2$ (J/g) |
|---|---|---|---|---|---|---|---|---|---|---|---|
| 75.3-24.7 | 48.9 | 51.1 | 1.31 | 6.2 | 4.1 | −20.7 | −40.0 | 58.4 | 45.7 | 39.2 | 18.7 |
| 76.5-23.5 | 51.4 | 48.6 | 1.13 | 6.4 | 3.9 | −22.1 | −38.9 | 57.4 | 45.7 | 42.1 | 21.3 |
| 79.2-20.8 | 57.0 | 43.0 | 1.61 | 7.6 | 4.0 | −24.1 | −42.6 | 53.7 | 45.0 | 44.3 | 26.2 |
| 51.7-48.3 | — | 100 | — | 2.4 | 4.1 | −13.9 | −11.3 | — | — | — | — |
| 100-0*) | — | — | — | — | — | −58.1 | −61.0 | 64.0 | 59.0 | 81.7 | 63.0 |

*)(Mn = 80000)

TABLE 3

Properties of segmented co-polyesters with PCL 4000 pre-polymer

| P(CL-DLLA) (mol %) | composition (% w/w) Cap4000 | dl-lac/cap 2000 | [η] | $\bar{L}_{Cap}$ | $\bar{L}_{Lac}$ | $Tg_1$ (°C.) | $Tg_2$ (°C.) | $Tm_1$ (°C.) | $Tm_2$ (°C.) | $\Delta H_1$ (J/g) | $\Delta H_2$ (J/g) |
|---|---|---|---|---|---|---|---|---|---|---|---|
| 62.2-37.8 | 18.9 | 83.1 | 2.35 | 3.3 | 4.0 | −20.8 | −23.9 | 38.7 | — | 8.8 | — |
| 67.4-32.6 | 28.4 | 71.6 | 1.00 | 4.1 | 4.0 | −17.7 | −31.1 | 56.9 | 46.2 | 25.1 | 4.2 |

TABLE 4

Properties of random co-polyesters

| P(CL-DLLA) (mol %) | M/I | [η] | $\bar{L}_{Cap}$ | $\bar{L}_{Lac}$ | $Tg_1$ (°C.) | $Tg_2$ (°C.) | $Tm_1$ (°C.) | $Tm_2$ (°C.) | $\Delta H_1$ (J/g) | $\Delta H_2$ (J/g) |
|---|---|---|---|---|---|---|---|---|---|---|
| 74.5-25.5 | 7200 | 3.12 | 4.0 | 2.9 | −39.3 | −38.9 | 42.4 | — | 9.0 | — |
| 77.5-22.5 | 8500 | 3.78 | 7.1 | 4.1 | −37.4 | −46.9 | 43.7 | 39.7 | 28.5 | 7.1 |
| 80.2-19.8 | 4650 | 2.18 | 5.2 | 2.6 | −37.3 | −42.7 | 42.0 | — | 20.2 | — |

TABLE 5

Molecular weights of phase separated, segmented co-polyesters measured by GPC

| P(CL-DLLA) (mol %) | PCL length | [η] | Mw (·10⁻³) | MN (·10⁻³) | D |
|---|---|---|---|---|---|
| 63.6-36.4 | 2000 | 3.62 | 234.0 | 117.3 | 2.0 |
| 74.6-25.4 | 2000 | 2.08 | 287.0 | 89.0 | 3.23 |
| 67.7-32.3 | 3000 | 1.99 | 171.9 | 83.3 | 2.07 |
| 75.3-24.7 | 3000 | 1.31 | 287.9 | 115.9 | 2.50 |

Results and Discussion

Summary:

Segmented co-polyesters build of a DL-lactide-ε-caprolactone soft segment (with Mn 2000) and of a PCL hard segment (with Mn 3000 or Mn 4000) and with a hard segment content of 33-57% and 28% (w/w), respectively, are flexible, thermoplastic elastomers with good mechanical and thermal properties. This type of material seems very promising for being used for nerve guides capable of bridging nerve defects larger than 2 cm.

As a reference material, random copolymers of D,L-Lactide and ε-caprolactone with similar monomer compositions as the segmented copolymers have been prepared. The lower degree of phase separation and the lower melting point of the crystalline phase makes them less applicable as polymers for biomedical devices. These differences are caused by a different monomer distribution: in a block-copolymer such as the phase separated lactide/ε-caprolactone based co-polyester, the average sequence length of the monomers will be longer and the sequence length distribution will be much smaller than in a 'random' copolymer. The average monomer sequence length will affect the thermal- and mechanical properties of the copolymer.

Results:

Phase separated segmented co-polyesters with structure (ab)r consisting of a poly-ε-caprolactone hard phase and a poly(DL-lactide-ε-caprolactone) soft phase have been prepared with various ratios of DL-lactide and ε-caprolactone. A non-random distribution of lactide and ε-caprolactone is obtained: the monomer sequence is determined by those of the individual building blocks. A small part of the poly(ε-caprolactone) prepolymer is amorphous and is present in the amorphous poly(lactide-ε-caprolactone) phase; the major part of the poly-ε-caprolactone is present as the crystalline hard phase. The degree of phase-mixing and the polymer properties are dependent on the pre-polymer chain length and -ratio.

Phase separation occurs above a certain threshold of the hard phase content. The content at which the hard phase is formed (crystallisation) is related to the molecular weight (chain length) of the pre-polymer(s). Segmented polyesters based on PCL (poly-ε-caprolactone) hard segments and lactide-ε-caprolactone soft segments and with Mn=2000 of the soft segment forming pre-polymer show a good phase separation with a pre-polymer content of 40-45% of the PCL hard segment forming phase with Mn=2000, 33% of a pre-polymer with Mn=3000, and 28% of a pre-polymer with Mn=4000, respectively. The longer PCL segment results in a better phase separation beginning at lower concentration. The effects of the composition of the segmented copolymers on the degree of phase separation are clarified by the thermal- and mechanical properties. FIGS. 2-6 show the differences in thermal properties and monomer distribution of segmented co-polyesters with soft segment pre-polymer length of 2000 and hard segment pre-polymer lengths of 2000 (cap2000) and 3000 (cap3000) and 4000 (cap4000), respectively. Also, the properties of the random poly(DL-lactide-ε-caprolactone) prepared at 120° C. during 5 days are shown. The glass transition temperature (Tg) of the soft segment in cap3000 and cap4000 is higher than that in cap2000 with a similar monomer ratio (FIG. 2): the amorphous phase of cap3000 and cap4000 contains less amorphous PCL than that of cap2000, due to a better phase separation. Both are higher than the values of Tg of the random copolymers with similar monomer composition. Furthermore, the higher the ε-caprolactone content within a copolymer range with the same PCL length, the lower the Tg will be, due to partly mixing of the amorphous PCL with the soft segment. In case of cap2000 and cap4000, the Tg of the copolymer with a low PCL content (23% and 19% w/w, respectively) is almost as low as the Tg measured in the second run, where the copolymer is completely amorphous. In general, in the second DSC run, the Tg decreases with ε-caprolactone content and is independent of the monomer distribution (segmented or random).

The melting points of the hard segment (Tm) are shown in FIG. 3. The melting point (maximum of melting peak) increases with ε-caprolactone content and is highest for the cap3000 series with a maximum value at a ε-caprolactone content of about 75%. A cap4000 copolymer with a caprolactone content of 67.4% has a much higher melting point than the cap3000 copolymer with a similar monomer composition. This is the result of a better phase separation of the longest PCL segment. The melting points with the highest ε-caprolactone content within the cap3000 series are somewhat lower than expected, probably caused by incomplete phase separation. The melting temperatures of the segmented copolymers with a large ε-caprolactone content are only a little lower than those of the PCL pre-polymer (58-60° C.) and of PCL with Mn=80000, having a Mp of 63° C. Melting points of the random copolymers are much lower (42-44° C.) than those of the segmented copolymers and are also much broader (the onset of the melting peak begins at 25-30° C.). This proves that there is a better phase separation in the segmented copolymers than in the random copolymers. In the second DSC run, melting temperatures of the segmented copolymers are lower (40-45° C.) due to incomplete phase separation. Re-crystallization does not occur at the lowest ε-caprolactone contents: the cap4000 copolymers start to re-crystallize at a lower ε-caprolactone content than the cap3000 and cap2000 copolymers. Therefore, the annealing time must be long enough to obtain complete phase separation. Melting temperatures of the random copolymers are also much lower (38-40° C.) or they are absent in the second run. These results are comparable to those found in literature (Lemmouchi et al., Hiljanen-Vainio et al.)

FIG. 4 shows the melting enthalpy (ΔH) of the three segmented copolymers and the random copolymer versus the ε-caprolactone content. The melting enthalpies of the cap3000 and cap4000 copolymers are largest and increase, both with the same trend, almost linearly with increasing ε-caprolactone content. A larger ε-caprolactone content leads to a larger melting enthalpy and therefore to a larger degree of crystallinity (as a reference, the melting enthalpy of the PCL pre-polymers is about 100 J/g).

The melting enthalpy of the random copolymers is not linearly dependent on the ε-caprolactone content. In fact, it is linearly related to the average monomer sequence length of ε-caprolactone, $\overline{L}_{Cap}$. FIG. 5 shows this relationship for the random- and segmented copolymers. Clearly, the cap3000 and cap4000 copolymers show larger melting enthalpies than the cap2000 and the random copolymers, at a similar average ε-caprolactone sequence length. In FIG. 6 it is shown that within the cap2000, cap3000 and cap4000 series, $\overline{L}_{Cap}$ increases with ε-caprolactone content, the relation being independent of the PCL length. However, this is not the case for the random copolymers. The monomer distribution is determined by the polymerisation conditions. The random copolymers are all prepared at the same polymerisation time and -temperature, but with a different catalyst concentrations. A lower catalyst concentration results in longer monomer sequence lengths and therefore, more crystallization occurs. The segmented copolymers are prepared by mixing of two pre-polymers: the average ε-caprolactone sequence length can be increased by adding more of the PCL pre-polymer. By this method, the average sequence length of lactide does not change and will be constant within a copolymer series (not shown). This means that during the short time of chain-extending, no trans-esterification reaction occurs and the final polymer properties are only dependent on the pre-polymer properties.

Concerning the thermal properties, the segmented copolymers are more suitable for biomedical applications than the random copolymers. Depending on the type of application, the monomer ratio can be changed while keeping the same thermal (and mechanical) properties simply by changing the length of the pre-polymers.

Mechanical Properties

Mechanical properties of the segmented copolymers are dependent on the degree of phase separation and therefore on the degree of crystallinity. As an example, the stress strain behavior of the segmented co-polyesters with the PCL pre-polymer with Mn=3000 is shown in FIG. 7. The stress at a certain degree of elongation (e.g 400%) increases with PCL content, so is the modulus. The tensile strength is also dependent on the amount of strain induced crystallization, which occurs when amorphous PCL starts to crystallize as a result of orientation. FIG. 8 presents the relation between the initial modulus and the ε-caprolactone content: the modulus of the PCL3000 containing copolymer is higher than that of the PCL2000 containing copolymer with the same ε-caprolactone content, as a result of the higher degree of crystallinity (melting enthalpy) of the former. The modulus of the random copolymers is variable with the ε-caprolactone content and can be as high as those of the segmented copolymers. In fact, the modulus is related to the average monomer sequence length, $\overline{L}_{Cap}$, a property that can be altered by varying the polymerisation conditions. In general, the modulus is related to the average monomer sequence length, $\overline{L}_{Cap}$, in the same way as is the melting enthalpy as has been shown in FIG. 5. Although, from a mechanical point of view, the random copolymers can be as good as the segmented copolymers, the thermal properties are inferior to those of the segmented copolymers.

The modulus of the segmented co-polyesters can be much higher than those of amorphous, lactide rich copolymers (e.g. poly(DL-lactide-ε-caprolactone) with a 50:50 monomer ratio has an elastic modulus of 1-2 MPa). Therefore, segmented copolymers, even with a rather low ε-caprolactone content, can be processed into materials with a high modulus. For an application such as an artificial nerve guide for bridging long nerve gaps, a modulus that is high enough to prevent compression of the nerve guide is required. This can be accomplished by using segmented co-polyesters.

Example 8

In this example various biodegradable phase separated multi-block co-polymers were synthesized and evaluated for their processing and controlled release characteristics. The polymers were composed of a crystalline ε-caprolactone-based hydrophobic hard segment with a melting point (Tm) and a hydrophilic polyethylene glycol (PEG)-based segment having a glass transition temperature (Tg) that was below body temperature under physiological conditions.

Materials and Methods

Synthesis of Pre-polymers for Hard Segment

Poly(ε-caprolactone) pre-polymer (Mn=4000) was synthesized as follows: ε-Caprolactone (Acros, Belgium) was dried over $CaH_2$ and distilled under reduced pressure in a nitrogen atmosphere. 158.58 grams (1.39 mol) distilled ε-Caprolactone was introduced into a three-necked bottle under nitrogen atmosphere. 3.66 grams (42.1 mmol) of 1,4-butanediol (Acros, distilled from 4 Å molecular sieves after drying for 8 hours) was added. 54.7 mg stannous octoate (Sigma Corp) was added (monomer/catalyst molar ratio=10600). The mixture was magnetically stirred and reacted at 140° C. during 71 hours. $^1$H-NMR showed 99.8% monomer conversion. The calculated molecular weight (Mn) from in-weights was 3990. Molecular weight could not be determined by $^1$H-NMR, since the peaks of BDO overlap with the peaks of CL.

Synthesis of Pre-polymers for Hydrophilic Segment

Poly(ε-caprolactone-co-polyethyleneglycol 1500) pre-polymer (Mn=2000) was synthesized as follows: 62.68 grams (0.549 mol) ε-Caprolactone (see example 1 for purification) was introduced into a three-necked bottle under nitrogen atmosphere. 189.70 grams (0.126 mmol) of polyethylene glycol MW 1500 was added. PEG had been dried the day before synthesis for 17 hours at 90° C. under vacuum. 23.8 mg of stannous octoate (Sigma Corp) was added (monomer/catalyst molar ratio=11500). The mixture was magnetically stirred and reacted at 130° C. during 164 hours. $^1$H-NMR showed 99.5% monomer conversion. The calculated molecular weight (Mn) from in-weights was 2000. Analysis with $^1$H-NMR showed a Mn of 1987, which agrees well with the molecule weight from in-weights. MDSC analysis showed a Tm of 46.3° C., attributed to the crystalline PEG chain. Note that the measurement was performed under dry conditions. In water, PEG is amorphous.

Poly(DL-Lactide-co-polyethyleneglycol 1500) pre-polymer (Mn=2000) was synthesized as follows: 82.48 grams (0.572 mol) of D,L-lactide was introduced into a three-necked bottle under nitrogen atmosphere and dried at 50° C. for 16 h under vacuum. 245.45 grams (0.164 mmol) of polyethylene glycol MW 1500 was added. PEG had been dried the day before synthesis for 17 hours at 90° C. under vacuum. 24.1 mg of stannous octoate (Sigma Corp) was added (monomer/catalyst molar ratio=12400). The mixture was magnetically stirred and reacted at 130° C. during 188 hours. $^1$H-NMR showed 94.4% monomer conversion. The calculated molecular weight (Mn) from in-weights was 2000. Analysis with $^1$H-NMR showed a Mn of 1842, which agrees reasonably well with the theoretical molecular weight of 1972 based on in-weights and monomer conversion. MDSC analysis showed a Tm of 32.72° C., attributed to the crystalline PEG chain and a Tg of −29.7° C., attributed to an amorphous phase consisting of poly(D,L-Lactide) and PEG. Note that the measurement was performed under dry conditions. In water, PEG is amorphous.

Synthesis of Multi-block Co-polymers

Multi-block copolymers were synthesized according to the following general procedure: The PCL pre-polymer (Mn 4000) and ε-caprolactone-co-PEG-co-ε-caprolactone or D,L-Lactide-co-PEG-co-D,L-Lactide pre-polymer (Mn 2000) were pre-heated to 70° C. until they became more liquid. The appropriate amounts of both pre-polymers were weighted into a glass ampoule supplied with nitrogen inlet and a mechanical stirrer. 1,4-Dioxane (Acros, distilled over sodium) was added to a polymer concentration of 30 wt % and the contents of the ampoule were heated to 80° C. to dissolve the prepolymers. 0.990 equivalent (with respect to the pre-polymer hydroxyl groups) of 1,4-butanediisocyanate (Bayer, distilled at reduced pressure) was added and the reaction mixture was stirred mechanically for 20-22 hours. Non-distilled dioxane was added to a polymer concentration of 20 wt % to quench unreacted isocyanate groups. The reaction mixture was further diluted with non-distilled dioxane to a polymer concentration of 10 wt %. The ampoule was cooled to room temperature, the reaction mixture was poured into tray and frozen at −18° C. Subsequently, dioxane was removed by placing the frozen reaction mixture under vacuum at 30° C. The polymer was stored in a sealed package at −18° C. A small part of the batch was analyzed for thermal properties (mDSC), dioxane content (gas chromatography), intrinsic viscosity and polymer composition ($^1$H-NMR).

30(ε-caprolactone-co-$PEG_{1500}$-ε-caprolactone)$_{2000}$-b-70 (ε-caprolactone)$_{4000}$ (30CLPEG15CL20-b-CL40) was synthesized as follows: 18.91 grams of PCL pre-polymer (Mn 3990, 4.74 mmol) and 8.00 grams of ε-caprolactone-co-$PEG_{1500}$-ε-caprolactone pre-polymer (Mn 2000, 4.00 mmol) were introduced into a three-necked bottle under nitrogen atmosphere. The three necked bottle was supplied with nitrogen inlet and a mechanical stirrer. 45 mL of 1,4-dioxane was added and the mixture was heated to 80° C. to dissolve the prepolymers. 1.2276 grams (8.76 mmol) of 1,4-butanediisocyanate was added (1.002 equivalent with respect to the pre-polymer hydroxyl groups) and 20 mL of 1,4-dioxane was used to flush the 1,4-diisocyanate bottle for quantitative addition of the 1,4-butanediisocyanate. Final polymer concentration was 30 wt %. The reaction mixture was stirred mechanically for 20 hours. 44 mL of non-distilled dioxane was added obtaining a polymer concentration of 20 wt % to quench unreacted isocyanate groups. The reaction mixture was further diluted with 137 mL of non-distilled dioxane obtaining a polymer concentration of 10 wt %. The three necked bottle was cooled to room temperature, the reaction mixture was poured into tray and frozen first at 4° C. and subsequently at −18° C. Subsequently, dioxane was removed by placing the frozen reaction mixture under vacuum at 30° C. The polymer was stored in a sealed package at −18° C. A small part of the batch was analyzed for thermal properties (mDSC), dioxane content (gas chromatography) intrinsic viscosity and polymer composition ($^1$H-NMR).

50(ε-caprolactone-co-$PEG_{1500}$-ε-caprolactone)$_{2000}$-b-50 (ε-caprolactone)$_{4000}$ (50CLPEG15CL20-b-CL40) was synthesized as follows: 25.33 grams of PCL pre-polymer (Mn 3990, 6.35 mmol) and 24.50 grams of ε-caprolactone-co-$PEG_{1500}$-ε-caprolactone pre-polymer (Mn 2000, 12.3 mmol) were introduced into a three-necked bottle under nitrogen atmosphere. The three necked bottle was supplied with nitrogen inlet and a mechanical stirrer. 95 mL of 1,4-Dioxane was added and the mixture was heated to 80° C. to dissolve the prepolymers. 2.6052 grams (18.59 mmol) of 1,4-butanediisocyanate was added (1.000 equivalent with respect to the pre-polymer hydroxyl groups) and 20 mL of 1,4-dioxane was used to flush the 1,4-diisocyanate bottle for quantitative addition of the 1,4-butanediisocyanate. Final polymer concentration was 30 wt %. The reaction mixture was stirred mechanically for 20.5 hours. 85 mL of non-distilled dioxane was added obtaining a polymer concentration of 20 wt % to quench unreacted isocyanate groups. The reaction mixture was further diluted with 240 mL of non-distilled dioxane obtaining a polymer concentration of 10 wt %. The three necked bottle was cooled to room temperature, the reaction mixture was poured into tray and frozen first at 4° C. and subsequently at −18° C. Subsequently, dioxane was removed by placing the frozen reaction mixture under vacuum at 30° C. The polymer was stored in a sealed package at −18° C. A small part of the batch was analyzed for thermal properties (mDSC), dioxane content (gas chromatography) intrinsic viscosity and polymer composition ($^1$H-NMR).

70(ε-caprolactone-co-$PEG_{1500}$-ε-caprolactone)$_{2000}$-b-30 (ε-caprolactone)$_{4000}$ (70CLPEG15CL20-b-CL40) was synthesized as follows: 13.93 grams of PCL pre-polymer (Mn 3990, 3.49 mmol) and 32.74 grams of ε-caprolactone-co-$PEG_{1500}$-ε-caprolactone pre-polymer (Mn 2000, 16.37 mmol) were introduced into a three-necked bottle under nitrogen atmosphere. The three necked bottle was supplied with nitrogen inlet and a mechanical stirrer. 92 mL of 1,4-Dioxane was added and the mixture was heated to 80° C. to dissolve the prepolymers. 2.6298 grams (18.77 mmol) of 1,4-butanediisocyanate was added (0.946 equivalent with respect to the prepolymer hydroxyl groups) and 20 mL of 1,4-dioxane was used to flush the 1,4-diisocyanate bottle for quantitative addition of the 1,4-butanediisocyanate. Final polymer concentration was 30 wt %. The reaction mixture was stirred mechanically for 20 hours. 79 mL of non-distilled dioxane was added obtaining a polymer concentration of 20 wt % to quench unreacted isocyanate groups. The reaction mixture was further diluted with 240 mL of non-distilled dioxane obtaining a polymer concentration of 10 wt %. The three necked bottle was cooled to room temperature, the reaction mixture was poured into tray and frozen first at 4° C. and subsequently at −18° C. Subsequently, dioxane was removed by placing the frozen reaction mixture under vacuum at 30° C. The polymer was stored in a sealed package at −18° C. A small part of the batch was analyzed for thermal properties (mDSC), dioxane content (gas chromatography) intrinsic viscosity and polymer composition ($^1$H-NMR).

50(D,L-lactide-co-$PEG_{1500}$-D,L-lactide)$_{2000}$-b-50(ε-caprolactone)$_{4000}$ (50LAPEG15LA20-b-CL40) was synthesized as follows: 23.49 grams of PCL pre-polymer (Mn 4000, 5.87 mmol) and 23.37 grams of D,L-Lactide-co-$PEG_{1500}$-D, L-Lactide pre-polymer (Mn 2000, 11.7 mmol) were introduced into a three-necked bottle under nitrogen atmosphere. 117 mL of 1,4-Dioxane was added obtaining a polymer concentration of 28 wt % and the contents of the three necked bottle were heated to 80° C. to dissolve the prepolymers. The three necked bottle was supplied with nitrogen inlet and a mechanical stirrer. 2.4325 grams (17.4 mmol) of 1,4-butanediisocyanate was added (0.989 equivalent with respect to the prepolymer hydroxyl groups). and then stirred mechanically for 21 hours. 85 mL of non-distilled dioxane was added obtaining a polymer concentration of 18 wt % to quench unreacted isocyanate groups. The reaction mixture was further diluted with 227 mL of non-distilled dioxane obtaining a polymer concentration of 9.6 wt %. The ampoule was cooled to room temperature, the reaction mixture was poured into tray and frozen first at 4° C. and subsequently at −18° C. Subsequently, dioxane was removed by placing the frozen reaction mixture under vacuum at 30° C. The polymer was stored in a sealed package at −18° C. A small part of the batch was analyzed for thermal properties (mDSC), dioxane content (gas chromatography) intrinsic viscosity and polymer composition ($^1$H-NMR).

Characterization of Multi-block Copolymers

Modulated Differential Scanning Calorimetry (mDSC): 5-15 mg of sample was weighed in a DSC pan. The measurements were performed on a DSC Q1000 (TA Instruments) using a modulated temperature program. Amplitude was set to 1° C., the modulation period to 60 s and the heating rate to 5° C./min. Samples were heated from −80° C. to 200° C. Samples were performed once or in duplicate. In case of duplicate measurements, average results were recorded.

$^1$H-Nuclear magnetic resonance: $^1$H-NMR was performed on a VXR Unity Plus NMR Machine (Varian) operating at 300 MHz. The $d_1$ waiting time was set to 20 sec, and the number of scans was 16-32. Spectra were recorded from 0 to 14 ppm. $^1$H-NMR samples were prepared by dissolving 10 mg of polymer into 1 mL of deuturated chloroform.

Intrinsic Viscosity (IV): Intrinsic viscosity was measured using an Ubbelohde Viscosimeter (DIN), type 0C, 0a or I, Schott Geräte supplied with a Schott AVS-450 Viscosimeter including a water bath. The measurements were performed in chloroform at room temperature. The polymer concentration in chloroform was such that the relative viscosity was in the range of 1.2 to 2.0.

Dioxane content: Dioxane content was determined using a GC-FID headspace method. Measurements were performed on a GC-FID Combi Sampler supplied with a Agilent Column, DB-624/30 m/0.53 mm. Samples were prepared in DMSO. Dioxane content was determined using dioxane calibration standards.

Swelling test: Polymer films were made by pouring a 13 wt % polymer solution in dichloromethane (DCM) (approx. 300 mg of polymer with 1.5 mL of DCM), on a glass plate and spreading the polymer solution with a casting knife. The DCM was left to evaporate slowly overnight and the residual DCM was removed by vacuum drying at 20° C. Resulting films had a thickness of 100-200 μm. For the swelling tests, 15-40 mg of circular films with a diameter of approximately 25 mm were weighed and immersed in a flask containing 10 mL of phosphate buffer pH 7.4 (ISO-15814). The samples were stored in an oven at 37° C. For each sampling point starting from t=0, the films were taken out of the buffer solution. The buffer solution at the surface of film was removed and the film was weighed on a 4-decimal balance. All tests were performed in duplicate.

Extrusion of Multi-block Copolymers

Small diameter implants of CLPEG15CL20-b-CL40 multi-block copolymer CLPEG15CL20-b-CL40 were prepared by extrusion of small amounts of copolymer at temperatures varying from 40 to 100° C. using a Haake Minilab extruder (Thermo Electron). Screw rotation rate, torque and temperature were recorded. Extruded strands were cut with a cutting device, visually examined and analyzed for their thermal characteristics and intrinsic viscosity.

Preparation of Protein-loaded Depot Formulations

To prepare protein-loaded films, 200 al of an aqueous protein (BSA or lysozyme) solution (200 mg/mL in water) was emulsified in a multi-block co-polymer solution in dichloromethane (1.5 mL, 13 wt. % polymer concentration) using ultraturrax-mixing (30 s at 16 k rpm). Polymer films were prepared by solvent casting and vacuum-drying procedures as used for the preparation of films for the swelling test.

For preparation of microspheres, two methods were used namely a standard solvent evaporation method and a membrane emulsification-based solvent evaporation method. The preparation of microspheres using the standard solvent evaporation was prepared using procedures described by Kissel et al., J. Controlled Release 39 (1996) p. 315-326 and Meinel et al., J. Controlled Release 70 (2001) p. 193-202. Multi-block co-polymers were dissolved in dichloromethane at concentrations of typically 15% w/v.

For the preparation of protein-loaded microspheres, first a water-in-oil emulsion was prepared. The protein (BSA or lysozyme) was dissolved in water to a concentration of about 150 mg/mL, and 0.15 mL of the protein solution was added to a solution of approximately 0.5 g polymer in 2 mL of dichloromethane. This mixture was homogenized for 60 seconds using an Ultraturrax IKA T18 operated at 20,000 rpm yielding a water-in-oil (W/O) emulsion. The W/O emulsion was subsequently added to 60 mL of an aqueous solution containing 4% w/v PVA and emulsified for 30 seconds using an Ultraturrax IKA T18 operated at 14,000 rpm yielding a water-in-oil-in water (W/O/W) emulsion. The obtained W/O/W emulsion was gently stirred mechanically. Due to the evaporation of the dichloromethane, the polymer precipitated from the solution to yield microspheres. After 3 hours (the time necessary to achieve almost complete evaporation of the dichloromethane) the formed microspheres were collected by centrifugation, washed with water (3 times) and finally lyophilized.

For preparation of monodisperse microspheres by the membrane emulsification-based solvent evaporation method similar methods were used with the difference that now the water-in-oil emulsion of protein and polymer was placed in a vessel containing a membrane with identically sized pores of approx. 11 micrometer. The W/O emulsion was forced through the membrane by applying pressure and fed into a stirred aqueous solution containing 4% w/v PVA. After 3 hours the formed monodisperse microspheres were collected and further treated as described above.

For the preparation of protein-loaded implants, a mixture of 1 to 20% w/w protein and 80-99% w/w CLPEG15CL20-b-CL40 multi-block copolymer were fed to the extruder and extruded at temperatures varying from 40 to 100° C. as described above. Extruded strands were cut with a cutting device.

For measuring the release of protein from the depot formulations, 15-25 mg of protein-loaded samples (films, microspheres or implants) were weighed and immersed in a flask containing 5 mL of phosphate buffer pH 7.4 (ISO-15814). The samples were stored in an oven at 37° C. At each sampling point 1 mL of supernatant was taken and refreshed by 1 mL of the phosphate buffer. The protein content in the samples was determined with a BCA assay using an Easys Expert 96 well plate reader.

Results

Characterization of Multi-block Copolymers

The synthesized multi-block copolymers were analyzed for their chemical composition, molecular weight and residual dioxane content. Table 6 shows the collected analysis results for multi-block copolymers 30CLPEG15CL20-b-CL40, 50CLPEG15CL20-b-CL40, 70CLPEG15CL20-b-CL40 and 50LAPEG15LA20-b-CL40. The actual composition of the copolymers, as determined by $^1$H NMR from the CL/PEG ratio resembled the target composition well. All polymers had an intrinsic viscosity between 0.4 and 1.5. Dioxane contents were below 1000 ppm indicating effective removal of dioxane by vacuum-drying.

TABLE 6

Collected results regarding the chemical composition, intrinsic viscosity and residual dioxane content of multi-block copolymers 30CLPEG15CL20-b-CL40, 50CLPEG15CL20-b-CL40, 70CLPEG15CL20-b-CL40 and 50LAPEG15LA20-b-CL40.

|  | 30CLPEG15CL20-b-CL40 | 50CLPEG15CL20-b-CL40 | 70CLPEG15CL20-b-CL40 | 50LAPEG15LA20-b-CL40 |
|---|---|---|---|---|
| Molar LA/PEG ratio in-weights | N.A. | N.A. | N.A. | 7.0 |
| Molar LA/PEG ratio $^1$H-NMR | N.A. | N.A. | N.A. | 6.2 |
| Molar CL/PEG ratio in-weights | 47.0 | 22.1 | 11.7 | 17.2 |
| Molar CL/PEG ratio $^1$H-NMR | 43.4 | 20.8 | 11.9 | 17.2 |
| Intrinsic viscosity (dL/g) | 0.69 | 0.74 | 1.45 | 0.43 |
| Dioxane content (ppm) | <1000 | <200 | <200 | <200 |

The synthesized multi-block copolymers were analyzed for their thermal properties to confirm their phase separated morphology. FIG. 9 shows typical DSC thermograms of 50CLPEG15CL20-b-CL40 and 50LAPEG15LA20-b-CL40 multi-block copolymers. All multi-block copolymers exhibited two distinct melting temperatures (Tm). The copolymers exhibited one Tm of approximately 52 to 56° C., which represents the melting temperature of poly(ε-caprolactone) and one significantly lower Tm between 10 and 30° C. representing the crystalline polyethylene glycol segment of prepolymer (A). As expected, the melting enthalpy of the crystalline poly(ε-caprolactone) increased with increasing amount of poly(ε-caprolactone) segment, whereas the melting enthalpy of the crystalline polyethylene glycol segment of prepolymer (A) decreased linearly with increasing amount of poly(ε-caprolactone) segment. The data clearly show the phase separated morphology of the copolymers. For all multi-block copolymers a glass transition temperature (Tg) was found around −50 to −60° C.

TABLE 7

Thermal characteristics of multi-block copolymers 30CLPEG15CL20-b-CL40, 50CLPEG15CL20-b-CL40, 70CLPEG15CL20-b-CL40 and 50LAPEG15LA20-b-CL40.

|  | 30CLPEG15CL20-b-CL40 | 50CLPEG15CL20-b-CL40 | 70CLPEG15CL20-b-CL40 | 50LAPEG15LA20-b-CL40 |
|---|---|---|---|---|
| Tg (° C.) | −58.5 | −57.8 | −57.2 | −52.5 |
| Tm (° C.) | 11.4/55.1 | 22.8/54.3 | 25.5/52.4 | 21.2/55.8 |
| ΔHm (J/g) | 11.7/68.5 | 30.0/56.7 | 47.4/28.2 | 35.1/39.9 |

Table 8 shows the swelling degree of the multi-block copolymers. The swelling degree was found to increase gradually with the content of polyethylene glycol of the copolymers.

TABLE 8

Composition and swelling of multi-block copolymers 30CLPEG15CL20-b-CL40, 50CLPEG15CL20-b-CL40 and 50LAPEG15LA20-b-CL40.

|  | Wt. % Segment A | Wt. % Segment B | MW PEG | Wt. % PEG | Swelling degree (—) |
|---|---|---|---|---|---|
| 30CLPEG15CL20-b-CL40 | 30 | 70 | 1500 | 22.5 | 1.20 |
| 50CLPEG15CL20-b-CL40 | 49 | 51 | 1500 | 37.5 | 1.45 |
| 70CLPEG15CL20-b-CL40 | 70 | 30 | 1500 | 52.5 | 1.80 |

Extrusion of Multi-block Co-polymers

Small diameter implants of CLPEG15CL20-b-CL40 multi-block copolymer CLPEG15CL20-b-CL40 were prepared. Surprisingly, despite the crystalline character of the polymers, their melting temperature of 50-55° C., and their relatively high intrinsic viscosity, the polymers could be easily extruded through a small diameter die of approximately 0.5 mm at a temperature as low as 40° C. and at acceptable torque and screw rotation rate. The obtained strand, which formed a colorless transparent strand upon leaving the die turned opaque after a few seconds, illustrating cooling-induced crystallization of the molten polymer. Due to its flexibility, the strand could easily be cut with a cutting device without formation of debris, which is typically encountered when cutting rigid polymeric strands such as extruded strands composed of PLGA. The capability of extrusion of the polymers at such low temperatures makes these polymers especially suitable for the incorporation of thermosensitive and labile active compounds such as biologically active peptides and proteins. Moreover, the formation of a semi-crystalline polymeric matrix with a Tm of 50-55 oC provides sufficient product stability during storage.

Polypeptide Release from Films

FIGS. 10 and 11 show the release of Lysozyme and BSA, respectively, from 30CLPEG15CL20-b-CL40, 50CLPEG15CL20-b-CL40, 70CLPEG15CL20-b-CL40 multi-block copolymers. The results clearly show that the rate at which the polypeptides are released from the polymer matrices increases with increasing PEG content and swelling degree. Surprisingly, the release of BSA from 50CLPEG15CL20-b-CL40 and 70CLPEG15CL20-b-CL40 multi-block copolymers was completely linear over extended periods of time up to more than 200 days for 50CLPEG15CL20-b-CL40.

Example 9

This Example describes the preparation of Lysozyme-containing small diameter implants by hot melt extrusion of powder mixtures of lysozyme with either 30CLP15CL20-b-C40 or standard poly(DL-lactide-co-glycolide) with IV 0.4 dl/g, and testing of the in vitro release kinetics of Lysozyme from the extrudates.

Methods

Lyophilized Lysozyme and 30CLP15CL20-b-C40 or PLGA5004 (protein:polymer ratio 1:9 w/w) were physically mixed in a mortar using a pestle and extruded at 55-60° C. (30CLP15CL20-b-C40) or 95° C. (PLGA5004) through a 0.5 mm die using a Haake MinilabII double screw extruder (Rheomex CTW5, Thermo Scientific) operated at a screw speed of 10-15 rpm. The diameter of the strand was controlled at 350 μm, using an inline lasermike. Extruded strands were collected and cut into uniform pieces of 10 mm length.

For content and content uniformity analysis, the extrudates were randomly collected at several time points during the extrusion run and lysozyme was extracted from individual implants by dissolution in ethyl acetate, followed by dissolution of the precipitate in PBS and lysozyme analysis by HPLC. For in vitro release, implants were incubated in 1.2 mL of 100 mM PBS, pH 7.4 at 37° C. in a shaking water bath. At each sampling point, 1 mL of PBS was removed and refreshed with PBS and Lysozyme content was determined with HPLC.

Results

Smooth extrudates with a diameter of 350 μm were obtained from the physical mixture of 30CLP15CL20-b-C40 and Lysozyme when extruded as described above. Scanning electron microscopy showed only some minor surface roughness (data not shown.

The Lysozyme content of the 30CLP15CL20-b-C40 extrudates as determined by extraction was 11.2 wt. %±1.5%, which was slightly higher than the target loading (10.0 wt. %). The low standard deviation indicates that the powder blend was well mixed in the extruder, leading to acceptable content uniformity.

In vitro release testing of Lysozyme from the extrudates shows a burst release of approximately 8% for both polymers. PLGA-based implants showed their typical biphasic release pattern with a plateau value with hardly any Lysozyme release up to 3 weeks. At three weeks lysozyme release rate increased due to degradation of the PLGA matrix. For 30CLP15CL20-b-C40 a slow but continuous release profile was obtained yielding a cumulative release of around 50% at 4 weeks (see FIG. 12). Based on these release kinetics and based on the low degradation rate of 30CLP15CL20-b-C40, a slow but continuous release of lysozyme lasting for around 3-4 months can be achieved.

REFERENCES

1. European patent application nr. 02075481.8: DL-Lactide-ε-caprolactone copolymers.
2. C. G. Pitt, M. M. Gratzl, G. L. Kimmel, J. Surles and A. Schindler, The degradation of poly(D,L-lactide), poly (ε-caprolactone) and their copolymers in vitro. *Biomaterials* 2 (1981) 215-220.
3. M. Malin, M. Hiljainen-Vainio, T. Karjalainen, J. Seppala, Biodegradable lactone copolymers II. Hydrolytic study of ε-caprolactone and lactide copolymers. *J. Appl. Polym. Sci.* 59 (1996) 1289-1298.
4. M. Hiljainen-Vainio, T. Karjalainen, J. Seppala, Biodegradable lactone copolymers. I. Characterisation and mechanical behaviour of ε-caprolactone and lactide copolymers. *J. Appl. Polym. Sci.* 59 (1996) 1281-1288.
5. Y. Lemmouchi, E. Schacht, P. Kageruka, R. De Deken, B. Diarra, O. Diall and S. Geerts, Biodegradable polyesters for controlled release of trypanocidal drugs: in vitro and in vivo studies. *Biomaterials* 19 (1998) 1827-1837.

The invention claimed is:

1. A composition for the controlled release of at least one biologically active polypeptide having a molecular weight equal to or greater than 10,000 to a host, comprising the at least one biologically active polypeptide encapsulated in a matrix comprising at least one phase separated, thermoplastic, biodegradable multi-block copolymer, the copolymer being characterized in that:
   (i) it comprises at least two hydrolysable segments chosen from prepolymer (A) and prepolymer (B), prepolymer (A) having a Tg lower than 37° C. and prepolymer (B) having a Tm of 40° C.-100° C. under human body conditions;
   (ii) the phase separated copolymer having at least two phase transitions, each of which is related to the corresponding Tg or Tm values of the prepolymers which are comprised in the copolymer;
   (iii) prepolymer (A) comprising reaction products of cyclic monomers selected from glycolide, lactide, ε-caprolactone, δ-valerolactone, trimethylene carbonate, tetramethylenecarbonate, 1,5-dioxepane-2-one, 1,4-dioxane-2-one (para-dioxanone) and/or cyclic anhydrides; and wherein prepolymer (A) contains a segment that is derived from a water soluble polymer derived from a diol, a diamine or a diacid;
   (iv) prepolymer (B) comprising poly(ε-caprolactone) with an Mn of larger than 3000;
   (v) the segments being linked by a diisocyanate chain-extender;
   (vi) the segments are randomly distributed over the polymer chain; and
   (vii) said copolymer contains poly(ethylene glycol), as a segment of pre polymer (A) and/or as an additional pre polymer, and wherein said poly(ethylene glycol)
      a) has a molecular weight of from about 600 to about 5000 g/mol, and
      b) is present in an amount of from about 5 wt. % to about 60 wt. %-based upon the total weight of the copolymer.

2. Composition according to claim 1, wherein said copolymer contains poly(ethylene glycol) as a segment of prepolymer (A).

3. Composition according to claim 1, wherein said poly (ethylene glycol) has a molecular weight of from about 1000 to about 3000 g/mol.

4. Composition according to claim 1, wherein said poly (ethylene glycol) is present in an amount of from about 10 wt. % to about 50 wt. %.

5. Composition according to claim 1, wherein a water soluble polymer is present as an additional prepolymer.

6. Composition according to claim 1, wherein said water soluble polymer is selected from the group consisting of polyethers, polyvinylalcohol (PVA) polyvinylpyrrolidone (PVP), polyvinylcarprolactam, poly(hydroxymethylmethacrylate) (poly-(HEMA)), polyphosphazenes, polyorthoesters, polyorthoesteramides or copolymers of the previous polymers.

7. Composition according to claim 6, wherein the polyethers are polyethylene glycol (PEG), polytetramethyleneoxide (PTMO), or polypropyleneglycol (PPG).

8. Composition according to claim 6, wherein said water soluble polymer is derived from PEG having a molecular weight of 150-5000.

9. Composition according to claim 1, wherein prepolymer (A) comprises reaction products of lactide or ε-caprolactone.

10. Composition according to claim 1, wherein said biologically active polypeptide is a biologically active peptide or biologically active protein.

11. Composition according to claim 10, wherein said biologically active polypeptide is a biologically active peptide or biologically active protein selected from the group consisting of protein/peptide drugs, enzymes, receptor ligands, neurotransmitters, inhibitory peptides, regulatory peptides, activator peptides, cytokines, growth factors, monoclonal antibodies, anti-tumour peptides, antibiotics, antigens, vaccines and hormones.

12. Composition according to claim 1, wherein said matrix is processed in the form of a microsphere, microparticle, implant, coating, gel, film, foil, sheet, rod, or membrane.

13. Composition according to claim 12, wherein said processing involves extrusion or injection moulding.

14. Composition according to claim 13, wherein said processing involves extrusion or injection moulding at a temperature from about 20° C. to 80° C.

15. Composition according to claim 14, wherein said processing involves extrusion or injection moulding at a temperature from about 30° C. to 60° C.

16. Composition according to claim 12, in the form of a coating and wherein said coating is applied as a drug-eluting coating on a medical implant.

17. Composition according to claim 16, wherein said medical implant is a vascular or urinary stent, an orthopaedic prosthesis or an ocular implant.

18. Composition according to claim 12, in the form of an implant.

19. Composition according to claim 18, wherein the implant is an injectable implant.

20. Composition according to claim 1, wherein the cyclic anhydride is oxepane-2,7-dione.

21. A method for delivering a biologically active polypeptide of interest to a subject in need thereof, comprising administering an effective dose of a composition according to claim 1 to said subject.

22. Method according to claim 21, wherein said administering comprises the parenteral, intra-arterial, intra-articular, intra-venal, intra-ocular, epidural, intrathecal, intra-muscular or subcutaneous administration of said composition.

23. Method according to claim 22, wherein the composition is in the form of microspheres, an injectable implant or an in situ forming gel.

24. Method according to claim 22, wherein said administration is intra-ocular, intramuscular or subcutaneous.

* * * * *